US 12,371,657 B2

(12) United States Patent
Dietz et al.

(10) Patent No.: US 12,371,657 B2
(45) Date of Patent: *Jul. 29, 2025

(54) CELL CULTURE MEDIA COMPOSITIONS FOR PRIMARY CELLS

(71) Applicant: Mayo Foundation for Medical Education and Research, Rochester, MN (US)

(72) Inventors: Allan B. Dietz, Chatfield, MN (US); Gaylord Knutson, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/545,335

(22) Filed: Dec. 19, 2023

(65) Prior Publication Data

US 2024/0158738 A1 May 16, 2024

Related U.S. Application Data

(62) Division of application No. 14/712,491, filed on May 14, 2015, now Pat. No. 11,891,620.

(60) Provisional application No. 61/994,637, filed on May 16, 2014.

(51) Int. Cl.
| | |
|---|---|
| C12N 5/00 | (2006.01) |
| A61K 35/19 | (2015.01) |
| A61P 17/02 | (2006.01) |
| C12N 5/071 | (2010.01) |
| C12N 5/0775 | (2010.01) |

(52) U.S. Cl.
CPC ............ *C12N 5/0037* (2013.01); *A61K 35/19* (2013.01); *A61P 17/02* (2018.01); *C12N 5/0068* (2013.01); *C12N 5/0662* (2013.01); *C12N 5/069* (2013.01); *C12N 5/0692* (2013.01); *C12N 2500/84* (2013.01); *C12N 2501/105* (2013.01); *C12N 2501/11* (2013.01); *C12N 2501/115* (2013.01); *C12N 2501/165* (2013.01); *C12N 2502/115* (2013.01); *C12N 2533/50* (2013.01); *C12N 2533/90* (2013.01)

(58) Field of Classification Search
CPC ........ C12N 5/0037; A61K 35/19; A61P 17/02
See application file for complete search history.

(56) References Cited

U.S. PATENT DOCUMENTS

| | | |
|---|---|---|
| 5,185,160 A | 2/1993 | Chao |
| 5,198,357 A | 3/1993 | Holmovist et al. |
| 5,292,362 A | 3/1994 | Bass et al. |
| 5,756,686 A | 5/1998 | Heldin et al. |
| 5,834,418 A | 11/1998 | Brazeau et al. |
| 7,335,508 B2 | 2/2008 | Yayon et al. |
| 8,361,796 B2 | 1/2013 | Menasche et al. |
| 8,501,170 B2 | 8/2013 | Rebulla et al. |
| 9,682,104 B2 | 6/2017 | Patel |
| 10,166,258 B2 | 1/2019 | Dietz et al. |
| 10,925,901 B2 | 2/2021 | Dietz et al. |
| 11,891,620 B2 | 2/2024 | Dietz et al. |
| 2004/0151709 A1 | 8/2004 | Gorrochategui Barrueta et al. |
| 2005/0214277 A1 | 9/2005 | Schaufler |
| 2006/0014266 A1 | 1/2006 | Tomasevic et al. |
| 2006/0142198 A1 | 6/2006 | Gandy |
| 2007/0184029 A1 | 8/2007 | Mishra |
| 2009/0023211 A1 | 1/2009 | Persson et al. |
| 2009/0305401 A1 | 12/2009 | Strunk et al. |
| 2010/0120144 A1 | 5/2010 | Mishra |
| 2011/0123498 A1 | 5/2011 | Westenfelder |
| 2011/0171731 A1 | 7/2011 | Dietz et al. |
| 2012/0156306 A1 | 6/2012 | Weissman et al. |
| 2013/0195959 A1 | 8/2013 | Patel |
| 2014/0335195 A1 | 11/2014 | Houze et al. |
| 2016/0074481 A1 | 3/2016 | Burnouf et al. |
| 2016/0082047 A1 | 3/2016 | Dietz et al. |
| 2017/0260496 A1 | 9/2017 | Dietz et al. |
| 2021/0154234 A1 | 5/2021 | Dietz et al. |

FOREIGN PATENT DOCUMENTS

| | | | | |
|---|---|---|---|---|
| AU | 2010202675 A1 | * | 2/2011 | ........... C12N 5/0037 |
| EP | 2 733 200 A1 | | 5/2014 | |
| WO | 89/10398 A1 | | 11/1989 | |
| WO | 95/15763 A1 | | 6/1995 | |
| WO | 2005/065419 A2 | | 7/2005 | |

(Continued)

OTHER PUBLICATIONS

U.S. Appl. No. 15/609,444 (Year: 2014).*
"Anticoagulant" https://en.wikipedia.org/wiki/Anticoagulant (Year: 2024).*
European Search Report for Application No. 09815127.7 mailed Dec. 13, 2012, 12 pages.
European Search Report for Application No. 16170752.6 mailed Aug. 29, 2016.
Extended European Search Report, EP Appln. No. 19181191.8, dated Nov. 26, 2019.

(Continued)

*Primary Examiner* — Ruth A Davis
(74) *Attorney, Agent, or Firm* — Merchant & Gould P.C.

(57) ABSTRACT

Platelet lysate compositions and cell culture media compositions for maintaining and/or growing mammalian cells, such as mammalian endothelial cells (ECs) and mammalian endothelial progenitor cells (EPCs), in particular human ECs (huECs) and human EPCs (huEPCs), such as primary huECs and primary huEPCs, are provided. The cell culture media compositions contain a basal medium, a platelet lysate and, optionally, one or more exogenously added growth factors. Also provided are methods for making and using such cell culture media compositions to grow and/or maintain ECs and EPCs, including huECs and huEPCs, as well as cell culture vessels, dishes, plates, and/or flasks pretreated with the cell culture media compositions.

14 Claims, 10 Drawing Sheets

(56) References Cited

FOREIGN PATENT DOCUMENTS

| WO | 2006/137778 A1 | 12/2006 |
|---|---|---|
| WO | 2008/034803 A1 | 3/2008 |
| WO | 2008/110570 A1 | 9/2008 |
| WO | 2009/002811 A2 | 12/2008 |
| WO | 2009/144718 A1 | 12/2009 |
| WO | 2010/017216 A2 | 2/2010 |
| WO | 2010/033605 A2 | 3/2010 |
| WO | 2010/033605 A3 | 3/2010 |
| WO | 2013/076507 A2 | 5/2013 |
| WO | 2013/113024 A1 | 8/2013 |
| WO | 2016/139340 A1 | 9/2016 |
| WO | 2016/193591 A1 | 12/2016 |

OTHER PUBLICATIONS

Faler et al., "Transforming Growth Factor-β and Wound Healing," Perspectives in Vascular Surgery and Endovascular Therapy, vol. 18, No. 1, pp. 55-62 (2006).
Fan et al., "Glioma stem cells: evidence and limitation," Semin Cancer Biol., 17(3):214-218 (2007).
Frank et al., "Regulation of Vascular Endothelial Growth Factor Expression in Cultured Keratinocytes," The Journal of Biological Chemistry, vol. 270, No. 21, pp. 12607-12613 (1995).
Freeze-Drying/Lyophilization of Pharmaceutical and Biological Products, Marcel Dekker, Inc., New York, New York, edited by Louis Rey and Joan C. May, 488 pages (1999).
Grounds of Appeal by Opponent for EP3095856 mailed Aug. 12, 2022.
Gruber et al., "Platelet-released supernatants increase migration and proliferation, and decrease osteogenic differentiation of bone marrow-derived mesenchymal progenitor cells under in vitro conditions," Platelets, 15(1):29-35 (2004).
Hara et al., "Platelets as a Source of Growth-Promoting Factors for Tumor Cells," Cancer Research, vol. 40, pp. 1212-1216 (1980).
Ho et al., "The behavior of human mesenchymal stem cells in 3D fibrin clots: dependence on fibrinogen concentration and clot structure," Tissue Eng., 12(6):1587-1595 (2006).
Hoffbauer et al., "Human platelet lysate is a a feasible candidate to replace fetal calf serum as medium supplement for blood vascular and lymphatic endothelial cells," International Society for Cellular Therapy, (2017).
Ihm et al., "Effects of mixed leukocyte reaction, hydrocortisone and cyclosporine on expression of leukocyte adhesion molecules by endothelial and mesangial cells," J Korean Med Sci., 11(6):495-500 (Dec. 1996).
International Preliminary Report on Patentability for PCT/US2009/057170, mailed Mar. 31, 2011, 8 pages.
International Preliminary Report on Patentability for PCT/US2015/030834 mailed Nov. 22, 2016, 12 pages.
International Search Report (partial) for corresponding PCT Patent Application No. PCT/US2015/030834 mailed Jul. 31, 2015.
International Search Report (partial) for corresponding PCT Patent Application No. PCT/US2015/030834 mailed Oct. 19, 2015.
International Search Report and Written Opinion for PCT/US2015/030834 mailed Oct. 19, 2015.
International Search Report and Written Opinion for PCT/US2009/057170, mailed May 10, 2010, 12 pages.
Janetzko et al., "Fully automated processing of buffy-coat-derived pooled platelet concentrates," Transfusion, vol. 44, pp. 1052-1058 (2004).
Janowska-Wieczorek et al., "Microvesicles derived from activated platelets induce metastasis and angiogenesis in lung cancer," Int J Cancer., 113(5):752-760 (2005).
Janowska-Wieczorek et al., "Enhancing effect of platelet-derived microvesicles on the invasive potential of breast cancer cells," Transfusion, 46(7):1199-1209 (Jul. 2006).

Jung et al., "Ex vivo expansion of human mesenchymal stem cells in defined serum-free media," Stem Cells Int., 2012:123030, 21 pgs (May 7, 2012).
Kitange et al., "Recent advances in the molecular genetics of primary gliomas," Curr Opin Oncol., 15(3):197-203 (2003).
Kocaoemer et al., "Human AB Serum and Thrombin-Activated Platelet-Rich Plasma are Suitable Alternatives to Fetal Calf Serum for the Expansion of Mesenchymal Stem Cells from Adipose Tissue," Stem Cells, vol. 25, pp. 1270-1278 (2007).
Labitzke et al., "A serum-free medium formulation supporting growth of human umbilical cord vein endothelial cells in long-term cultivation," Cytotechnology, 35(2):87-92 (Mar. 2001).
Lange et al., "Platelet lysate for rapid expansion of human mesenchymal stromal cells," Cell Ther Transplant., 1 (2):49-53 (2008).
Le Bras et al., "Fibroblast Growth Factor 2 Promotes Pancreatic Epithelial Cell Proliferation Via Functional Fibroblast Growth Factor Receptors During Embryonic Life," Diabetes, vol. 47, pp. 1236-1242 (1998).
Lee et al., "Tumor stem cells derived from glioblastomas cultured in bFGF and EGF more closely mirror the phenotype and genotype of primary tumors than do serum-cultured cell lines," Cancer Cell, 9(5):391-403 (2006).
Lindroos et al., "Differential gene expression in adipose stem cells cultured in allogeneic human serum versus fetal bovine serum," Tissue Eng Part A., 16(7):2281-2294 (Jul. 2010).
Linkhart et al., "Growth Factors for Bone Growth and Repair: IGF, TGFβ and BMP," Bone, vol. 19, No. 1, Supplement, pp. 1S-12S (Jul. 1996).
Lucarelli et al., "Platelet-derived growth factors enhance proliferation of human stromal stem cells," Biomaterials, 24(18):3095-3100 (2003).
Macopharma, "Testing of platelet lysate derived from platelet concentrate" MacoProductions (Apr. 2, 2009).
Mariluz et al., "Serum-converted platelet lysate can substitute for fetal bovine serum in human mesenchymal stromal cell cultures," Cyrotherapy (2013), 15, pp. 1458-1468.
Marquez-Curtis et al., "Microvesicles derived from activated platelets enhance the invasive potential of breast cancer cells," Blood (ASH Annual Meeting Abstracts) 104: Abstract 3904 (2004).
Martineau et al., "Effects of calcium and thrombin on growth factor release from platelet concentrates: kinetics and regulation of endothelial cell proliferation," Biomaterials, 25(18):4489-4502 (2004).
Minutes and Interloctury Decision with Enclosures for Application No. 09815127.7 mailed Dec. 6, 2018.
Minutes of Oral Proceedings for EP3095856 mailed Mar. 30, 2022.
Mojica-Henshaw et al., "Serum-converted platelet lysate can substitute for fetal bovine serum in human mesenchymal stromal cell cultures," Cyrotherapy, 15, pp. 1458-1468 (2013).
Naaijkens et al., "Human platelet lysate as a fetal bovine serum substitute improves human adipose-derived stromal cell culture for future cardiac repair applications," Cell Tissue Res., 348(1):119-130, Epub (Mar. 7, 2012).
Ogawa et al., "Production of macromolecular activators of phagocytosis by lysed platelets," Thromb Res., 97(5):297-306 (2000).
Piccirillo et al., "Brain tumour stem cells: possibilities of new therapeutic strategies," Expert Opin Biol Ther., 7 (8):1129-1135 (2007).
Preliminary Opinion of the Board of Appeal for 3095856 mailed Dec. 8, 2023.
Protein Complex, Wikipedia, https://en.wikipedia.org/wiki/Protein_complex, 6 pages (Aug. 11, 2019).
Proulx et al., "Optimization of culture conditions for porcine corneal endothelial cells," Mol Vis., 13:524-533 (Apr. 3, 2007).
Ranzato et al., "Platelet lysate Stimulates Wound Repair of HaCaT keratinocytes," British Journal of Dermatology, vol. 159, pp. 537-545 (2008).
Rauch et al., "Alternatives to the Use of Fetal Bovine Serum: Human Platelet Lysates as a Serum Substitute in Cell Culture Media" Division of Physiology, Innsbruck Medical University, Innsbruck, Austria; Central Institute of Blood Transfusion and Immunology, University Hospital, Innsbruck Austria (2011).
Reddoch et al., Hemostatic Function of Apheresis Platelets Stored at 4C and 22C, Shock, vol. 41, Supplement 1, p. 54-61 (2014).

(56) References Cited

OTHER PUBLICATIONS

Reply Brief of Maco Pharma in the opposition of EP2334785, dated Oct. 20, 2017.
Reply of Maco Pharma to the Summons to Oral Proceedings of EP3095856 mailed Apr. 30, 2021.
Extended European Search Report for Application No. 24151761.4 mailed May 2, 2024.
Acid-base homeosttasis, Wikipedia, https://en.wikipedia.org/wiki/Acid-base_homeostasis, 7 pages (Jan. 2, 2020).
Anitua et al., "Autologous preparations rich in growth factors promote proliferation and induce VEGF and HGF production by human tendon cells in culture," Journal of Orthopaedic Research, vol. 23, pp. 281-297 (2005).
Arora, "Cell Culture Media: A Review," Mater Methods, 3:175 (2013).
Attachment to Brief in Opposition of EP2334785 entitled Testing of Platelet Lysate Derived from Platelet Concentrate (Apr. 2, 2009), filed by Maco Pharma, dated Feb. 24, 2017 (french/english version attached).
Australian Examination Report for Application No. 2015259094 mailed Aug. 21, 2020.
Australian Examination Report No. 2 for Application No. 2015259094 mailed May 11, 2021.
Australian Examination Report No. 2 for Application No. 2021277734 mailed Dec. 22, 2022.
Barano et al., "Serum-Free Medium Enhances Growth and Differentiation of Cultured Pig Granulosa Cells," Endocrinology, vol. 116, No. 1, pp. 51-58 (1985).
Barsotti et al., "Effect of platelet lysate on human cells involved in different phases of wound healing," PLoS One, 8 (12):e84753 (Dec. 27, 2013).
Bates et al., "The Role of Vascular Endothelial Growth Factor in Wound Healing," Lower Extremity Wounds, vol. 2, No. 2, pp. 107-120 (2003).
Bernardi et al., "The production method affects the efficacy of platelet derivatives to expand mesenchymal stromal cells in vitro," J. Tarnsl. Med. 15:90, 10 pages (2017).
Bernardo et al., "Optimization of in vitro expansion of human multipotent mesenchymal stromal cells for cell-therapy approaches: further insights in the search for a fetal calf serum substitute," J. of Cell. Physiol., 211(1):121-130 (2007) (Abstract only).
Bieback et al., "Clinical Protocols for the Isolation and Expansion of Mesenchymal Stromal Cells," Transfus Medicine and Hemotherapy, vol. 35, pp. 286-294 (2008).
Brief in Opposition of EP2334785, filed by Maco Pharma, dated Feb. 24, 2017 (french/english version attached).
Brief in Opposition of EP3095856, filed by Maco Pharma mailed May 13, 2020 (french/english version attached).
Brindley et al., "Peak serum: implications of serum supply for cell therapy manufacturing," Regen Med., 7(1):7-13 (Jan. 2012).
Brunner et al., "Serum-free Cell Culture: The Serum-free Media Interactive Online Database," Altex, 27(1):53-62 (2010).
Canadian Examination Report for Application No. 2,949,225 mailed May 18, 2021.
Canadian Examination Report for Application No. 2,949,225 mailed Jun. 8, 2022.
Canadian Examination Report for Application No. 2,949,225 mailed Aug. 18, 2023.
Canadian Examination Report for Application No. 3,138,143 mailed Dec. 1, 2022.
Capelli et al., "Human platelet lysate allows expansion and clinical grade production of mesenchymal stromal cells from small samples of bone marrow aspirates or marrow filter washouts," Bone Marrow Transplant., 40(8):785-791 (2007).
Carrancio et al., "Optimization of mesenchymal stem cell expansion procedures by cell separation and culture conditions modification," Experimental Menatology, vol. 36, pp. 1014-1021 (2008).
Chase et al., "A novel serum-free medium for the expansion of human mesenchymal stem cells," Stem Cell Res Ther., 1(1):8, (Apr. 2, 2010).
Cohen et al., "Insulin-Like Growth Factors (IGFs), IGF Receptors, and IGF-Binding Proteins in Primary Cultures of Prostate Epithelial Cells," Journal of Clinical Endocrinology and Metabolism, vol. 73, No. 2, pp. 401-407 (1991).
Communication of a notice of opposition of EP2334785, dated Mar. 13, 2017.
Communication of a notice of opposition of EP3095856 mailed May 19, 2020.
Communication pursuant to Rule 114(2) EPC, enclosing Third party observations, dated Apr. 25, 2018.
Communication pursuant to Rule 114(2) EPC, enclosing Third party observations for Application No. 09815127.7 mailed Sep. 1, 2015.
Communication Pursuant to Article 94(3) EPC, regarding EP Application No. 09815127.7 mailed Mar. 17, 2015.
Communication Pursuant to Article 94(3) EPC, regarding EP Application No. 09815127.7 mailed May 29, 2015.
Communication Pursuant to Article 94(3) EPC, regarding EP Application No. 09815127.7 mailed Nov. 10, 2015.
Communication Pursuant to Article 94(3) EPC, regarding EP Application No. 16170752.6 mailed Jul. 20, 2017.
Communication Pursuant to Article 94(3) EPC, regarding EP Application No. 15729597.3, dated Jul. 10, 2018.
Communication Pursuant to Article 94(3) EPC, regarding EP Application No. 15729597.3, dated Mar. 20, 2020.
Communication Pursuant to Article 94(3) EPC, regarding EP Application No. 19181191.8 mailed Mar. 16, 2021.
Communication Pursuant to Article 94(3) EPC, regarding EP Application No. 15729597.3 mailed Aug. 10, 2021.
Communication Pursuant to Article 94(3) EPC, regarding EP Application No. 19181191.8 mailed Mar. 28, 2022.
Communication Pursuant to Article 94(3) EPC, regarding EP Application No. 19181191.8 mailed Apr. 19, 2023.
Communication Regarding Oral Proceedings for Application No. 15729597.3 mailed Jul. 31, 2023.
Cowan et al., "Stimulation of human tumor colony formation by platelet lysate," J. Lab. Clin. Med., vol. 102, No. 6, pp. 973-986 (1983).
Crespo-Diaz et al., "Platelet Lysate Consisting of a Natural Repair Proteome Supports Human Mesenchymal Stem Cell Proliferation and Chromosomal Stability," Cell Transplantation, vol. 20, pp. 797-811 (2011).
Cryocheck, "Platelet Lysate" Intended use and instruction sheet; 1 page. Printed on Oct. 26, 2014 from Cryopep website at http://cryopep.com/cryocheck-platelet-lysate/.
Decision Rejecting the Opposition Against EP3095856 mailed Mar. 30, 2022.
Dietz et al., "A novel source of viable peripheral blood mononuclear cells from leukoreduction system chambers," Transfusion, 46(12):2083-2089 (2006).
Doucet et al., "Platelet Lysates Promote Mesenchymal Stem Cell Expansion: A Safety Substitute for Animal Serum in Cell-Based Therapy Applications," Journal of Cellular Physiology, 205:228-236 (2005).
Eastment et al., "Platelet Derived Growth Factor(s) for a Hormone-responsive Rat Mammary Tumor Cell Line," Journal of Cullular Physiology, vol. 97, No. 1, pp. 17-28 (1978).
EDQM, "Guide to the preparation, use and quality assurance of Blood Components," European Committee (Partial Agreement on Blood Transfusion (CD-P-TS), 2015).
"EGM-2 Endothelial Cell Growth Medium-2 BulletKit" Pharma & Biotech, retriefed from the Internet: https://bioscience.lonza.com/lonza_bs/en/Primary--Stem-Cells/p/000000000000185303/EGM-2-Endothelial-Cell-Growth-Medium-2-BulletKit (retrieved on Jul. 4, 2018).
EPO Communication forwarding Opponent's Submission Reply for EP3095856 mailed Jun. 6, 2023.
Canadian Examination Report for Application No. 3,138,143 mailed Apr. 26, 2024.
Horsch et al., "Evaluation of basal membrane-derived and biomaterial matrices for endothelial cell expansion and maintenance of their primitive potentialm," Journal of Stem Cells and Regenerative Medicine, vol. 6, No. 2, p. 104 (Oct. 2013).

(56) References Cited

OTHER PUBLICATIONS

Leotot et al., "Platelet lysate coating on scaffolds directly and indirectly enhances cell migration, improving bone and blood vessel formation," Acta Biomaterialia, vol. 9, pp. 6630-6640 (2013).
Walenda et al., "Human Platelet Lysate Gel Provides a Novel Three Dimensional-Matrix for Enhanced Culture Expansion of Mesenchymal Stromal Cells," Tissue Engineering: Part C, vol. 18, No. 12, pp. 924-934, DOI: 10.1089/ten.tec.2011.0541 (2012).
Reply to Observations made by the Patent Proprieter in EP3095856 mailed Jul. 30, 2021.
Reply to the Grounds of Appeal by Proprietor for EP3095856 including Auxiliary Requests mailed Dec. 13, 2022.
Response to Preliminary Opinion for EP3095856 mailed Feb. 23, 2024.
Saline (medicine), Wikipedia, https://en.wikipedia.org/wiki/Saline_(medicine), 8 pages (Dec. 30, 2019).
Schallmoser et al., "Generation of a pool of human platelet lysate and efficient use in cell culture," Methods Mol Biol., 946:349-62 (2013).
Sell et al., "Incorporating Platelet-Rich Plasma into Electrospun Scaffolds for Tissue Engineering Applications"; Tissue Engineering: Part A; 17(21-22):2723-2737 (Nov. 1, 2011).
Selvaggi et al., "Development of antibodies to fetal calf serum with arthus-like reactions in human immunodeficiency virus-infected patients given syngeneic lymphocyte infusions," Blood, 89(3):776-779 (Feb. 1, 1997).
Singh et al., "Identification of a cancer stem cell in human brain tumors," Cancer Res., 63(18):5821-5828 (2003).
Stacey et al., "Randomised Double-blind Placebo Controlled Trial of Topical Autologous Platelet Lysate in Venous Ulcer Healing," Eur. J. Vasc. Endovasc. Surg., vol. 20, pp. 296-301 (2000).
Submission in Response to Opponent Submission of Apr. 26, 2021 of EP3095856 mailed Jun. 1, 2021.
Submission by Opponent in Reply to last submission of Jun. 1, 2021 for EP3095856 mailed Jul. 30, 2021.
Submission in Reply to notice of opposition of EP2334785 with accompanying auxiliary requests, dated Aug. 9, 2017.
Submission in Reply to notice of opposition of EP3095856 with accompanying auxiliary requests dated Oct. 19, 2020.
Submission in Response to Summons to Attend Oral Proceedings, EP Appln. No. 09 815 127.7, dated Aug. 10, 2018.
Summons to attend oral proceedings regarding opposition of EP2334785, dated Dec. 20, 2017.
Summons to attend oral proceedings for Application No. 15729597.3 mailed Apr. 11, 2023.
Summons to attend oral proceedings regarding opposition of EP3095856 mailed Apr. 7, 2021.
Swope et al., "Long-Term Proliferation of Human Melanocytes is Supported by the Physiologic Mitogens α-Melanotropin, Endothelin-1, and Basic Fibroblast Growth Factor," Experimental Cell Research, vol. 217, pp. 453-459 (1995).
Tekkatte et al., 'Humanized' stem cell culture techniques: the animal serum controversy, Stem Cells Int., 2011:504723, Epub (Apr. 3, 2011).
Vogel et al., "Platelet-rich plasma improves expansion of human mesenchymal stem cells and retains differentiation capacity and in vivo bone formation in calcium phosphate ceramics," Platelets, 17(7):462-469 (Nov. 2006).
Wang, "Lyophilization and development of solid protein pharmaceuticals," Int J Pharm. ; 203(1-2): 1-60 (Aug. 2000).
Wang et al., "Platelet-induced inhibition of tumor cell growth," Thromb Res., 123:324-330 (2008).
Weibrich et al., "Growth factor levels in platelet-rich plasma and correlations with donor age, sex, and platelet count," J Craniomaxillofac Surg., 30:97-102 (2002).
WHO Technical Report, Series 924, 75 pages (2004).
Willey et al., Bombesin and the C-Terminal Tetradecapeptide of Gastrin-releasing Peptide are Growth Factors for Normal Human Bronchial Epithelial Cells, Experimental Cell Research, vol. 153, pp. 245-248 (1984).
Zimmermann et al., "Different preparation methods to obtain platelet components as a source of growth factors for local application," Transfusion, vol. 41, pp. 1217-1224 (2001).

\* cited by examiner

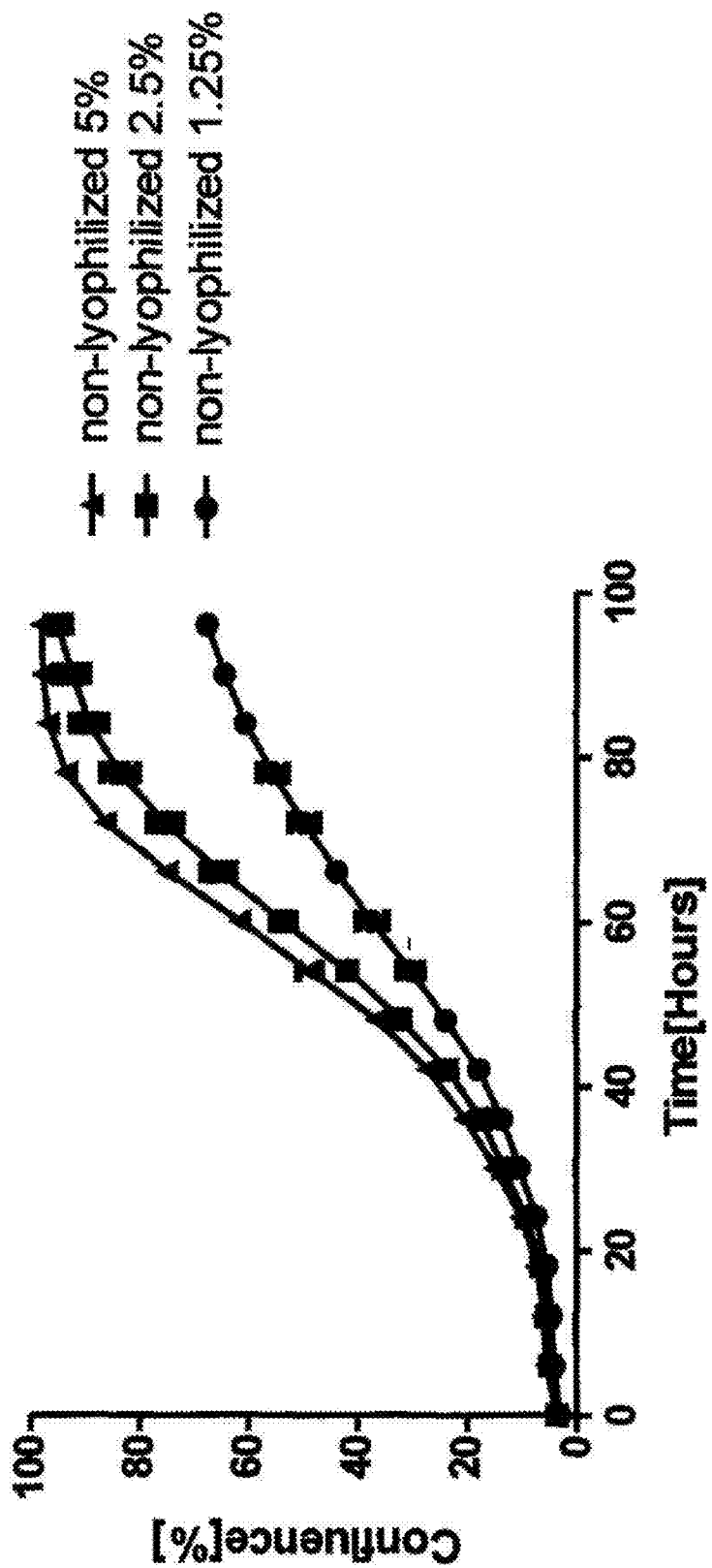

CELL CULTURE MEDIA COMPOSITIONS FOR PRIMARY CELLS

CROSS-REFERENCE TO RELATED APPLICATIONS

This application is a divisional of U.S. patent application Ser. No. 14/712,491 filed May 14, 2015, now issued as U.S. Pat. No. 11,891,620, which claims priority to U.S. patent application Ser. No. 61/994,637, filed May 16, 2014, the contents of all of which are hereby incorporated by reference in their entireties.

FIELD OF THE DISCLOSURE

The present disclosure relates, generally, to the culture of eukaryotic cells, in particular mammalian cells, including human cells. Cell culture media compositions for maintaining and/or growing mammalian cells, such as mammalian endothelial cells (ECs) and mammalian endothelial progenitor cells (EPCs), in particular human ECs (huECs) and human EPCs (huEPCs), such as primary huECs and primary huEPCs, are provided. The cell culture media compositions contain a product derived from human platelets. Methods for making and using such cell culture media compositions as well as cell culture dishes, plates, and/or flasks pretreated with the cell culture media compositions are provided and can be employed for the maintenance and/or growth of ECs and EPCs, including huECs and huEPCs.

BACKGROUND

Endothelial cells (ECs) line the interior surface of blood vessels and lymphatic vessels and form an interface between circulating blood or lymph in the lumen and the rest of the vessel wall. Endothelial progenitor cells (EPC) are a population of circulating cells in the blood that can differentiate into EC. EC and their progenitor cells play a wide variety of critical roles in the control of vascular function and participate to all aspects of the vascular homeostasis. For example, EC are critical players in fundamental physiological and pathological processes such as blood vessel formation, coagulation, fibribolysis, and the regulation of vascular tone as well as their participation in inflammatory reactions and in tumor neoangiogenesis.

Due to their importance, EC are routinely studied in both research laboratories and in clinical settings for a variety of diseases including cardiovascular disease, diabetes, cancer, and wound healing. For example, primary human EC have been routinely cultured to study the molecular pathways of EC biology. Cultured primary EC are diverse in biology, morphology, and growth characteristics depending on the source of EC. Commonly used primary EC are isolated from umbilical vein (HUVEC), aorta (aortic EC), coronary arteries (coronary arterial EC), lung (pulmonary EC) and microvascular EC. Culturing primary ECs is challenging because these cells have a relatively short life-span in vitro and because they tend to lose their primary characteristics and responsiveness to various stimuli beyond certain passage number (e.g., approximately 6-15 passages for HUVEC). Thus, there is great need for standardized, reproducible culturing conditions that can enhance the growth, prolong the life span and maintain the characteristics of primary EC.

Two methods are generally used to maintain primary ECs and tissues containing ECs in vitro and ex vivo. The commonly-used EC culture media for laboratory research involve supplementation of animal serum to provide growth factors for cell growth. Fetal bovine serum (FBS) is the most widely used serum-supplement due to its low level of antibodies and high level of growth factors. However, the use of animal derived serum, such as FBS, for culturing EC has the following limitations. First, serum is an ill-defined medium supplement, and thus an "X factor" in cell culture. Second, serum products usually exhibit high batch-to-batch variability, both quantitative and qualitative, which is detrimental for both research and clinical needs. Third, serum from xenogenic sources are potential sources of infectious and non-infectious pathogens such as viruses and prions. Fourth, serum may contain endotoxins, hemoglobins, and other adverse factors. Fifth, serum is prone to microbial contamination, such as viruses, prions, bacteria, nanobacteria, etc. Sixth, serum contains antibodies which may pose immunogenicity problems for cultured human cells. Finally, FBS and animal sera in general are expensive and the methods for harvesting blood (cardiac puncture from live animals without anesthesia) raise animal welfare concerns.

Therapies based on cells cultured in vitro or ex vivo (e.g., cell therapy, transplantation of engineered tissues) must meet stringent safety requirement for clinical use. Materials used for cell culture need to be approved for in vivo human use and need to be processed under GMP guidelines. Efforts geared toward reducing or eliminating animal-derived ingredients have positive safety and supply-chain implications. For at least these reasons, it is desirable to manufacture products intended for human use in animal origin-free reagents. The employment of xenogenic protein-free reagents would greatly reduce the chances of contamination of the cultured cells, with particular concern regarding *mycoplasma* and prions. Although FBS is approved for culturing cells for clinical cell therapy by the FDA, this is mainly a reflection of the lack of alternative animal-free and serum-free cell culture products. Cell culture products that are free of animal sera, capable of achieving high growth rates for primary EC, and manufactured under clinically-approved standards are needed.

SUMMARY

Lyophilized compositions, Cell culture media, kits, and methods of culturing cells in the media are provided herein. In embodiments, the lyophilized compositions, cell culture media, kits, and methods are designed to provide for enhanced growth of endothelial cells.

In one aspect, the disclosure describes a lyophilized composition comprising a platelet lysate and a physiological acceptable carrier. In embodiments, the lyophilized composition does not include a supplemental bulking agent, such as sucrose, mannitol, or trehalose. In embodiments, the physiological carrier is phosphate buffered saline. In embodiments, a physiological acceptable carrier is a basal medium. In embodiments, the lyophilized composition further comprises a supplemental growth factor. In embodiments, the supplemental growth factor is present in the composition in a ratio of at least 2000 to 1 per ng or less of the same growth factor present in the platelet lysate or per ng of FGF in the platelet lysate. In embodiments, the platelet lysate composition includes a single supplemental growth factor and does not include other supplemental growth factors, such as VEGF. In embodiments, the platelet lysate composition includes an anticoagulant. In embodiments, the lyophilized composition has about 50%, 40%, 30%, 20%, 10%, 5%, 2%, or 1% less water content. In embodiments, the lyophilized composition has a shelf life of at least 6 months.

In embodiments, the platelet lysate is lyophilized and comprises from about 50 to about 225 pg/ml FGF-B, from about 1 to about 10 ng/ml EGF, from about 5 to about 30 ng/ml PDGF-BB, from about 50 to about 150 ng/ml IGF-1, from about 50 to about 175 ng/ml TGF-β, and/or from about 300 pg/ml to about 1100 pg/ml VEGF and/or at least 30 mg of protein upon reconstitution in a 1 ml volume. In embodiments, the lyophilized platelet lysate is reconstituted in water, cell culture media, or a pharmaceutically acceptable carrier. In embodiments the lyophilized composition has a water content of 50% or less and is reconstituted in an aqueous carrier containing sufficient calcium to form a gel. In embodiments, the amount of calcium is at least 0.1 mM, or at least about 0.1 mM to about 100 mM. In embodiments, the lyophilized composition comprises an anticoagulant. In embodiments, the lyophilized platelet lysate does not include an exogenously added bulking agent such as sucrose, trehalose, and/or mannitol. In embodiments, the lyophilized platelet lysate does not include fetal bovine serum or other animal serum. In embodiments, a solid substrate is coated with a liquid or lyophilized platelet lysate.

A cell culture medium composition for culturing cells is disclosed. The cell culture medium can be used to culture endothelial cells (ECs) and endothelial progenitor cells (EPCs). The cell culture medium comprises a basal medium and a platelet lysate (PL). The PL can be human PL. In some embodiments, the PL comprises a filtrate of a lysed human apheresis platelet preparation. The concentration of PL in the basal medium can be between about 2% to 99%, 10% to 99%, 25% to 99%, or 50% to about 99% (v/v), depending on the application of the final media. In some embodiments, PL comprises from about 2% to about 10% (v/v) of the cell culture medium composition. In embodiments, the cell culture composition does not include fetal bovine serum or other animal serum.

The PL can include one or more growth factors, including but not limited to fibroblast growth factor (FGF-B), epidermal growth factor (EGF), platelet derived growth factor (PDGF), insulin-like growth factor (IGF), transforming growth factor (TGF), vascular endothelial growth factor (VEGF), liver growth factor (LGF), bone morphogenetic protein (BMP), colony stimulating factor (CSF), hepatocyte growth factor (HGF), nerve growth factor (NGF), and combinations thereof. In an embodiment, the PL comprises a concentration of VEGF of at least 200 pg/ml. In other embodiments, the PL comprises from about 50 to about 225 pg/ml FGF-B, from about 1 to about 10 ng/ml EGF, from about 5 to about 30 ng/ml PDGF-BB, from about 50 to about 150 ng/ml IGF-1, from about 50 to about 175 ng/ml TGF-β, and/or from about 300 pg/ml to about 1100 pg/ml VEGF.

The basal medium can include ingredients supporting cell growth, including, but not limited to, amino acids, vitamins, salts and other nutrients such as glucose. The cell culture medium can also be supplemented with one or more supplemental growth factors. These growth factors include, but are not limited to, FGF-B, EGF, PDGF, IGF, TGF, VEGF, LGF, BMP, CSF, HGF, NGF, and combinations thereof. In embodiments, a single supplemental growth factor is added to the cell culture composition, and other supplemental growth factors are not added to the cell culture supplement. In embodiments, the supplemental growth factors can be purified proteins or recombinant proteins.

In embodiments, the supplemental growth factor is added to cell culture medium containing platelet lysate or added to the platelet lysate compositions as described herein in order to enhance the growth in culture of a particular cell type, for example, a primary endothelial cell type. In embodiments, for use with endothelial cell culture, the supplemental growth factor is FGF-B. In embodiments, for use with endothelial cell culture, the supplemental growth factor added is FGF-B of at least 1 ng/ml, or at least about 1 to 100 ng/ml, or 1 to 50 ng/ml., or 1 to 10 ng/ml. in addition to the amount of FGF-B present in the platelet lysate of about 0.050 to about 0.225 ng/ml FGF-B. In embodiments, the supplemental exogenous FGF-B added is at least about 1 to 2000 fold, 1 to 1000 fold, or 1 to 100 fold greater than ng of FGF in the platelet lysate. In embodiments, another supplemental growth factor such as VEGF is not added to the platelet lysate or cell culture composition. In embodiments, the cell culture composition does not contain any fetal bovine serum or other animal serum.

In embodiments, for use with epithelial cell culture, the supplemental growth factor is EGF. In embodiments, for use with epithelial cell culture, the supplemental growth factor added is EGF of at least 1 ng/ml, or at least about 1 to 100 ng/ml, or 1 to 50 ng/ml., or 1 to 10 ng/ml. in addition to the amount of EGF present in the platelet lysate of. In embodiments, the supplemental exogenous EGF added is at least about 1 to 2000 fold, 1 to 1000 fold, or 1 to 100 fold greater than ng of EGF in the platelet lysate. In embodiments, another supplemental growth factor such as VEGF is not added to the platelet lysate or cell culture composition. In embodiments, the cell culture composition does not contain any fetal bovine serum or other animal serum.

In embodiments, for use with osteoblast cell culture, the supplemental growth factor is selected from the group consisting of IGF, TGF-β, BMP and combinations thereof. In embodiments, for use with osteoblast cell culture, the supplemental growth factor added is at least 1 ng/ml, or at least about 1 to 100 ng/ml, or 1 to 50 ng/ml., or 1 to 10 ng/ml. in addition to the amount of growth factor present in the platelet lysate. In embodiments, the supplemental exogenous growth factor(s) added is at least about 1 to 2000 fold, 1 to 1000 fold, or 1 to 100 fold greater than ng of growth factor in the platelet lysate. In embodiments, another supplemental growth factor such as VEGF is not added to the platelet lysate or cell culture composition. In embodiments, the cell culture composition does not contain any fetal bovine serum or other animal serum.

In embodiments, for use with melanocyte cell culture, the supplemental growth factor is selected from the group consisting of melanotropin, endothelin, TGFβ, and combinations thereof. In embodiments, for use with melanocyte cell culture, the supplemental growth factor added is at least 1 ng/ml, or at least about 1 to 100 ng/ml, or 1 to 50 ng/ml., or 1 to 10 ng/ml. in addition to the amount of growth factor present in the platelet lysate. In embodiments, the supplemental exogenous growth factor(s) is at least about 1 to 2000 fold, 1 to 1000 fold, or 1 to 100 fold greater than ng of growth factor(s) in the platelet lysate. In embodiments, another supplemental growth factor such as VEGF is not added to the platelet lysate or cell culture composition. In embodiments, the cell culture composition does not contain any fetal bovine serum or other animal serum.

In embodiments, the cell culture composition comprises an anti-coagulant, such as heparin, heparin derivatives, EDTA, citrate and oxalate.

Methods of culturing primary cells, such as ECs and/or EPCs, using the cell culture medium of the disclosure are also disclosed. The methods generally include plating ECs or EPCs in a cell culture medium composition under conditions that promote the growth and/or maintenance of said ECs or said EPCs. In some embodiments, the ECs are human primary ECs, including, but not limited to, umbilical vein ECs (hUVECs), microvascular ECs (hMVECs), aortic ECs (hAECs), saphenous vein ECs (hSVECs), or corneal epithelial cells (hCECs).

Tissue culture vessels, cell culture vessels, scaffolds, and supports comprising a coating of PL composition are also disclosed. Vessels, supports, and scaffolds coated with the PL of the disclosure can support the growth of cells. For example, PL coated vessels, supports, and scaffolds can be used to culture primary cells, such as EC and/or EPC in vitro. The PL coating can be supplemented with one or more supplemental growth factors. These growth factors include, but are not limited to, fibroblast growth factor (FGF-B), epidermal growth factor (EGF), platelet derived growth factor (PDGF), insulin-like growth factor (IGF), transforming growth factor (TGF), vascular endothelial growth factor (VEGF), liver growth factor (LGF), bone morphogenetic protein (BMP), colony stimulating factor (CSF), hepatocyte growth factor (HGF), nerve growth factor (NGF), and combinations thereof. In some embodiments, the vessels, supports, and/or scaffolds are treated with PL comprising a filtrate of a lysed human apheresis platelet preparation. In embodiments, a basal medium can be added to a culture vessel coated with PL to form a cell culture medium composition in the culture vessel for culturing EC or EPC. In embodiments, a lyophilized composition is dried onto a solid substrate. In some cases, the solid substrate is a cell culture plate, a glass bead, a mesh, a wound covering, and a stent. In embodiments, the lyophilized composition is combined with a collagen or fibrin gel.

Another aspect of the disclosure is directed to a wound healing composition. In embodiments, a wound healing composition comprises a lyophilized platelet lysate having 50% or less of water, a supplemental growth factor in a ratio of at least 100 to 1 per ng of growth factor in the platelet lysate, an anticoagulant, and about 0.1 mM to 100 mM calcium.

Another aspect of the disclosure includes methods of culturing cells in the cell culture composition described herein. In embodiments, a method comprises culturing ECs in a cell culture medium composition as described herein under conditions that promote the growth and/or maintenance of said ECs or said EPCs. In embodiments, a method comprises providing a cell culture vessel coated with a lyophilized composition comprising platelet lysate and a supplemental growth factor, adding basal medium to the cell culture vessel, adding endothelial cells and incubating the cells under conditions to reach at least 80% confluence. In embodiments, the cells are primary endothelial cells and cell numbers increase at least 2 fold in about 1 day, 2 days, 3 days 4, or 5 days of cell culture. In embodiments, fetal bovine serum is not added to the cell culture.

BRIEF DESCRIPTION OF THE DRAWINGS

FIG. 6A is a graph of percent confluence as a function of time (from 0 to 100 hours) for mesenchymal stem cells (MSCs) plated onto 48-well plates containing advance MEM with GlutaMAX, heparin, and penicillin/streptomycin further supplemented with PL (non-lyophilized) at concentrations of 5% (v/v) (▲), 2.5% (v/v) (■), and 1.25% (v/v) (●).

DETAILED DESCRIPTION

Figure 1:
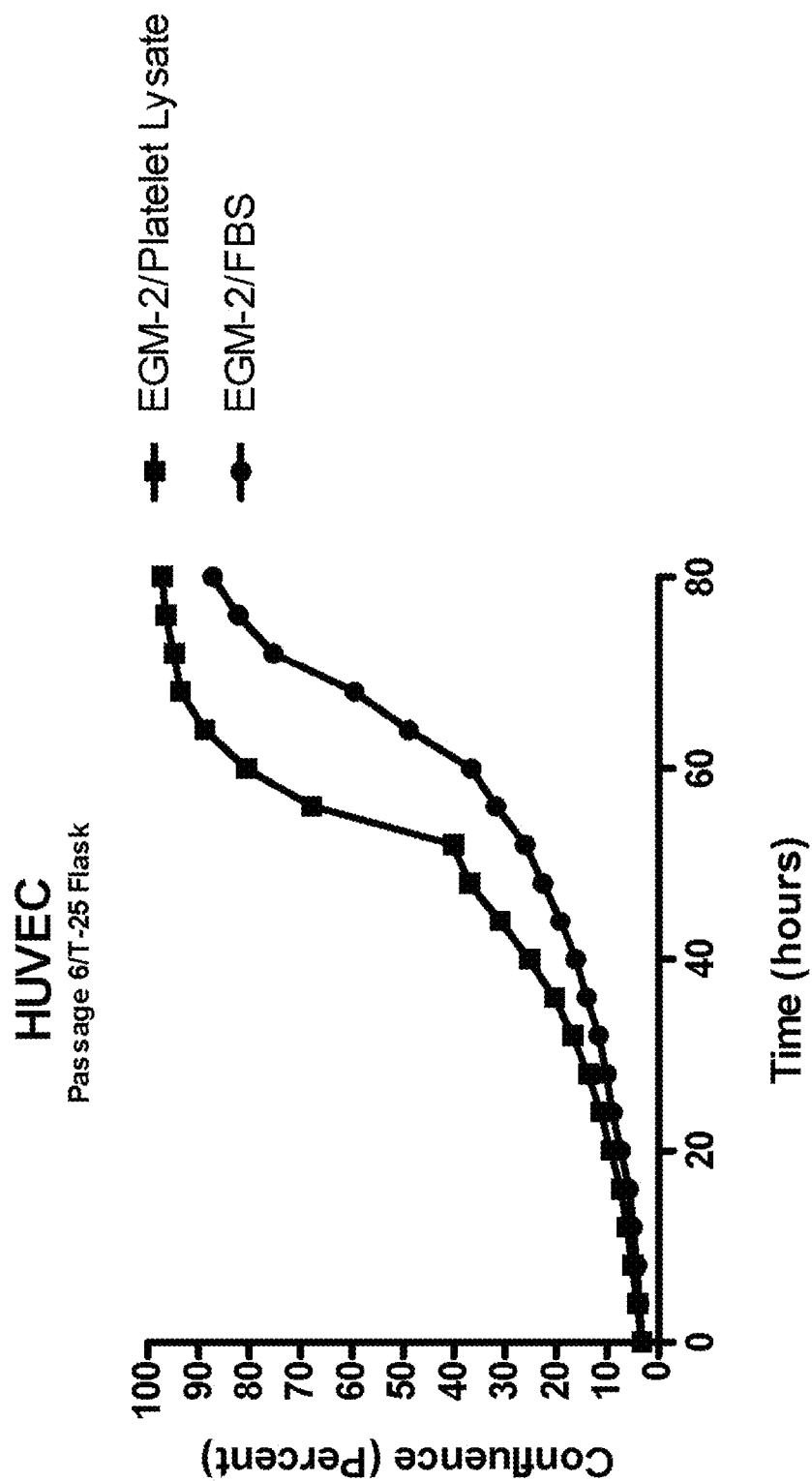
FIG. 1 is a graph of percent confluence as a function of time (from 0 to 80 hours) for human umbilical vein endothelial cells (HUVEC) seeded into flasks containing EGM™-2 media 20 supplemented with PL (■) or FBS (●), which demonstrates the superior growth rate of HUVECs grown in EGM™-2/PL as compared to EGM™-2/FBS.

The use of animal sera in the culturing of cells for therapeutic use in humans has raised safety concerns as the animal sera is prone to contamination by viruses, *mycoplasma*, prions, and bacteria and contain antibodies which may pose immunogenicity problems for cultured human cells.

For human somatic cell therapy and gene therapy products, the FDA is requiring the establishment of acceptance criteria for all media and components, including validation of serum additives and growth factors, as well as verification of freedom from adventitious agents. For manufacturers utilizing cell lines for the production of biologics, the FDA is requiring that the cells lines be certified to be free from contaminants and adventitious agents, such as the agent responsible for the production of Bovine Spongiform Encephalopathy, if serum or additives derived from animal sources are added to the cell culture medium. For cells to be administered to humans, the FDA recommends avoiding the use of any serum unless it can be shown that serum is required for cell activation. If the use of animal serum is necessary, the FDA recommends utilizing procedures for the inactivation of potential pathogens, such as heat and irradiation. Thus, the FDA is establishing a regulatory environment that clearly favors animal free, cell culture media compositions that have more defined components and lesser risk for carrying infectious disease agents.

The present disclosure is based upon the discovery that cell culture media, such as a basal medium or restrictive basal medium, which are supplemented with a human platelet lysate (PL) and, optionally, one or more supplemental growth factors, such as one or more of basic fibroblast growth factor (FGF-B), epidermal growth factor (EGF), vascular endothelial growth factor (VEGF), platelet derived growth factor (PDGF), can support the growth characteristics of cells, including human cells, such as human endothelial cells, human endothelial progenitor cells, human epithelial cells, human osteoblasts, and human melanocytes. The growth characteristics are substantially identical to the growth characteristics of those cells in culture cell media, including basal culture cell media, which are supplemented with a serum, such as fetal bovine serum (FBS; a/k/a fetal calf serum (FCS)) and/or one or more additional components such as one or more of the nine components of the SingleQuots™ basal media supplement (Lonza, Basel Switzerland).

The cell culture media compositions and platelet lysate compositions disclosed herein provide a solution that can meet the rising demand for cell culture products suitable for cell therapy and are capable of complying with the regulatory environment for such products. The cell culture media compositions comprise a cell culture medium, such as a basal medium or a restrictive basal medium basal medium; a human platelet lysate (PL) composition; and, optionally, one or more additional supplemental growth factors including, for example, basic fibroblast growth factor (FGF-B), epidermal growth factor (EGF), platelet-derived growth factor (PDGF), insulin-like growth factor (IGF), transforming growth factor (TGF), vascular endothelial growth factor (VEGF), or combinations thereof. In embodiments, the cell culture medium composition does not include fetal bovine serum and/or other animal serum.

The cell culture media compositions of the disclosure can be used to culture primary human cells, in particular endothelial cells and stem cells, as an alternative to cell culture media containing animal serum. The media compositions are capable of maintaining high growth rates for primary EC, free of animal sera, and can be manufactured under clinically-approved standards. Compared to animal derived serums, such as FBS, the platelet lysate in the media is of human origin and can be obtained from outdated/surplus platelet or whole blood from blood centers as described herein. The human platelet lysate can be produced from a pool of donors which allows advance production of a clinical good manufacturing practice (cGMP)-approved product without extensive testing.

Another aspect of the disclosure is methods for making the cell culture media compositions of the disclosure. The methods generally include adding a human platelet lysate (PL) to a cell culture medium, such as a basal medium or a restrictive basal medium, and, optionally, adding to the cell culture medium one or more additional or supplemental growth factors including, for example, basic fibroblast growth factor (FGF-B), epidermal growth factor (EGF), platelet derived growth factor (PDGF), insulin-like growth factor (IGF), transforming growth factor TGF), vascular endothelial growth factor (VEGF), liver growth factor (LGF), hepatocyte growth factor (HGF), nerve growth factor (NGF), or a combination thereof.

Another aspect of the disclosure is methods for maintaining and/or growing a cell, including a human cell, such as a human endothelial cell or a human endothelial progenitor cell, in particular a primary human endothelial cell or a primary human endothelial progenitor cell in culture. The methods generally include plating or seeding such a cell in a cell culture media composition comprising a cell culture medium, such as a basal medium or a restrictive basal medium; a human platelet lysate (PL); and, optionally, one or more additional supplemental growth factors including, for example, FGF-B, EGF, PDGF, IGF, TGF, VEGF, LGF, HGF, NGF, or a combination thereof.

Another aspect of the disclosure is lyophilized PL. The PL of the disclosure was unexpectedly found to retain its growth enhancement properties after lyophilization. Although lyophilization is a useful technique for single recombinant proteins, the ability to lyophilize a complex protein mixture such as PL that retains its growth properties after lyophilization was unexpected and surprising.

Another aspect of the disclosure is tissue culture vessels (e.g., plates, flasks, dishes, wells, tubes, coverslips, chambers, and/or bottles) and scaffolds (e.g., native or fabricated extracellular matrices) for culturing a cell, including a human cell, such as a human endothelial cell or a human endothelial progenitor cell, in particular a primary human endothelial cell or a primary human endothelial progenitor cell in culture. The tissue culture vessel and/or scaffold is treated with a platelet lysate composition or a cell culture media composition comprising a cell culture medium, such as a basal medium or a restrictive basal medium; a human platelet lysate (PL); and, optionally, one or more additional supplemental growth factors including, for example, FGF-B, EGF, PDGF, IGF, TGF, VEGF, LGF, HGF, NGF, or a combination thereof.

These and other aspects of the present disclosure will be better understood in view of the following non-limiting definitions:

Definitions

As used herein, the term "endothelial cell" or "EC" refers to a multifunctional cell type that forms the inner layer of blood vessels, including arteries, veins, and capillaries. The term "endothelial progenitor cell" or "EPC" refers to a cell that circulates in the blood that is programmed to differentiate into an "endothelial cell."

ECs provide an anticoagulant-mediated permeability barrier between vessel walls and blood or lymph. ECs also perform critical basal and inducible metabolic and synthetic functions. ECs react with physical and chemical stimuli within the circulating blood and lymph and regulate hemostasis, vasomotor tone, and immune and inflammatory responses. EC also play a pivotal role in angiogenesis and vasculogenesis—the development of new blood vessels for tissue repair or tumor growth. EC injury, activation, and/or dysfunction is a hallmark of many pathologic states including, for example, atherosclerosis, loss of semi-permeable membrane function, and thrombosis.

EC and EPC have broad applications in research and therapy. Cultured EC have been used in cell therapy methodology for the treatment of a wide variety of diseases including, for example, vascular diseases, heart disease, stroke, and eye diseases. Primary human EC are usually obtained by enzymatically dissociating, for example through trypsin-mediated proteolysis, EC from other cells in a tissue. Primary human EC are available from the American Type Culture Collection (ATCC), can be obtained from commercial providers including Lonza (Walkersville, MD) and PromoCell (Heidelberg, Germany), and can be isolated from human tissues and organs by those of skill in the art.

Primary EC that are commonly used for research and in clinical settings include, for example: (a) human umbilical vein EC (HUVEC), (b) human microvascular EC (HMVEC), (c) human aortic EC (HAEC), (d) human saphenous vein EC (HSVEC), and (e) human corneal epithelial cells (HCEC).

As used herein, the term "human umbilical vein EC (HUVEC)" refers to endothelial cells that are isolated from the endothelium of umbilical cord veins. HUVEC are the most commonly used model system for the study of the function and pathology of endothelial cells.

As used herein, the term "human microvascular EC (HMVEC)" refers to microvasculature endothelial cells that are isolated from a variety of tissues such as skin, lung, bladder, uterus, retina, and adipose. HMVEC are commonly used as a model system for the study of microvascular biology and diseases.

As used herein, the term "human aortic EC (HAEC)" refers to endothelial cells that are isolated from human aorta. HAEC are commonly used as a model system for the study of arteriosclerosis and arterial endothelial dysfunction.

As used herein, the term "human saphenous vein EC (HSVEC)" refers to endothelial cells that are isolated from human saphenous veins, which are often used for autotransplantation in coronary artery bypass operations when arterial grafts are not available or when many grafts are required. HSVEC are commonly used as a model system for the study of venous atherosclerosis and endothelial dysfunction.

As used herein, the term "human corneal epithelial cells (HCEC)" refers to epithelial cells isolated from human cornea. HCEC are commonly used for the in vitro study of corneal biology. HCEC can also be cultured for use in corneal reconstruction.

As used herein, the term "cell culture" refers to the ex vivo or in vitro maintenance and growth of cells, such as human or other mammalian cells, including, for example, primary human or other mammalian cells, as exemplified herein by primary human endothelial cells (hECs) and primary human endothelial progenitor cells (hEPCs) as described herein. Depending upon the conditions under which cells are cultured, cultured cells may grow/proliferate without differentiation into one or more organized tissues via synchronous mitotic cell division.

As used herein, the term "cell culture media" refers to solutions that contain factors and nutrients including, for example, growth factors, energy sources, amino acids, and organic and inorganic salts, which are used for the maintenance and growth of cells in ex vivo or in vitro culture. "Cell culture media" are often buffered to an approximately neutral pH (e.g., a pH of from about pH 6.6 to about pH 7.8) and can be supplemented with one or more antibiotics to prevent the growth of a bacterial and/or fungal contaminant.

As used herein, the terms "basal medium" or "restrictive basal medium" refers to compositions or solutions that contain at least essential amino acids, an energy source (e.g. a carbohydrate), vitamins, inorganic compounds (e.g. salts such as sodium chloride, and sodium phosphate), and one or more nucleotides which supplies energy and building materials for cell growth and proliferation. "Basal media" usually contain essential and nonessential amino acids, nucleobases, vitamins, glucose and other energy sources and inorganic salts. "Basal medium" or "restrictive basal medium" usually do not, however, contain growth factors or cytokines.

As used herein, the term "cell culture medium supplement" refers to a component or mixture of components that are added to a cell culture medium, such as a basal cell culture medium to facilitate the maintenance and/or growth of a cell plated and/or seeded in such a supplemented cell culture medium. A cell culture medium supplement may be in a liquid for or may be lyophilized prior to use to promote the stability and shelf-life of the individual supplement components. Cell culture medium supplements include, for example, growth factors, hormones (e.g., the glucocorticoid hydrocortisone), cytokines that promote the maintenance and/or growth of a cell, anti-oxidants, ribonucleotides, deoxyribonucleotides, anti-coagulants, sera, and/or antibiotics. Cell culture medium supplements are commonly added to a cell culture medium, such as a basal medium or a restrictive basal medium, immediately or shortly before use. One example of a commercially available cell culture medium supplement for culturing EC and EPC is SingleQuots™ (Lonza Walkersville, Inc. (Walkersville, MD)), which contains: (a) the growth factors human epidermal growth factor (EGF), human basic fibroblast growth factor (FGF-B), human vascular endothelial growth factor (VEGF), human long R3 insulin-like growth factor-1 (IGF-1); (b) the steroid hormone hydrocortisone; (c) the antioxidant ascorbic acid; (d) the anti-coagulant heparin; and (e) the antibiotics penicillin and streptomycin.

Cell culture medium supplements for culture of endothelial cells and endothelial progenitor cells can include one or more sera. As used herein, the terms "serum" and "sera" refer to the liquid portion of blood/plasma, which is typically also devoid of fibrinogen. Fetal bovine serum (FBS; a/k/a fetal calf serum (FCS)) is a common component of traditional EC growth media. It is usually added at low concentration (i.e., from about 2% (v/v) to about 5% (v/v)) to basal media that are specifically formulated for EC (e.g., MCDB-131 and EGM™-2) and at high concentrations (i.e., from about 10% (v/v) to about 30% (v/v)) to minimal basal media (e.g., DMEM/F-12 and M199). Animal serum is, however, incompatible with cGMP growth methods, thus limiting the clinical application of ECs that are cultured in media containing animal serum, and as such are not included in some embodiments of cell culture media described herein.

As used herein, the term "growth factor" refers to a protein or class of proteins, capable of stimulating cellular growth, cellular proliferation, cellular differentiation, and/or cellular maturation, such as, for example, EC proliferation and/or EPC differentiation. The term "growth factor" includes fragments of a protein capable of stimulating cellular growth, cellular proliferation, cellular differentiation, and/or cellular maturation. Examples of growth factors include, but are not limited to, basic fibroblast growth factor (FGF), epidermal growth factor (EGF), hepatocyte growth factor (HGF), nerve growth factor (NGF), platelet-derived growth factor-BB (PDGF-BB), long R3 insulin-like growth factor-1 (IGF-1), transforming growth factor beta (TGF-0), vascular endothelial growth factor (VEGF), bone morphogenetic proteins (BMP), and liver growth factor (LGF).

As used herein, the term "complete cell culture medium" or "cell culture medium composition" refers to cell culture medium that can support the maintenance and/or growth of cells in vitro or ex vivo.

As used herein, the term "maintenance of cells" refers to an extended period of cell survival without an increase or decrease in cell number.

As used herein the terms "growth" and "proliferation" are used interchangeably and refer to increase in cell numbers that results from the process of mitotic cell division. The growth/proliferation of cells may be detected by seeding/plating the cells in predetermined number/density and counting the cell numbers at different time points after seeding/plating. Cell growth/proliferation can be confirmed by monitoring cell density or confluence.

As used herein, the term "confluence" refers to the coverage of the surface of a cell culture vessel (e.g., cell culture plate, dish or flask) by cells. "Confluence" is usually calculated as percentage of available surface area of a cell culture vessel that is covered by cells. Cell confluence can be determined by employing an IncuCyte FLR Instrument (Essen Instruments Inc., Ann Arbor, MI) as used herein.

As used herein the phrase "pharmaceutically acceptable carrier" means a pharmaceutically acceptable material, composition or vehicle, such as a diluent or solvent. Each carrier must be "acceptable" in the sense of being compatible with the other ingredients of the composition and not injurious to the patient. Some examples of materials which may serve as pharmaceutically acceptable carriers include: magnesium hydroxide and aluminum hydroxide; alginic acid; pyrogen-free water; isotonic saline; Ringer's solution; basal medium; phosphate buffer solutions; silica gel; and other non-toxic compatible substances employed in pharmaceutical compositions.

As used herein, "supplemental" refers to a component of a composition that is added to a composition, regardless of whether some amount of the component is present in another component of the composition. For example, platelet lysate, one component of a composition, includes growth factors. A supplemental growth factor is an amount of a growth factor that is added to the composition over and above that found in the platelet lysate.

It will be understood that, unless indicated to the contrary, terms intended to be "open" (e.g., the term "including" should be interpreted as "including but not limited to," the term "having" should be interpreted as "having at least," the term "includes" should be interpreted as "includes but is not limited to," etc.). Phrases such as "at least one," and "one or more," and terms such as "a" or "an" include both the singular and the plural.

It will be further understood that where features or aspects of the disclosure are described in terms of Markush groups, the disclosure is also intended to be described in terms of any individual member or subgroup of members of the Markush group. Similarly, all ranges disclosed herein also encompass all possible sub-ranges and combinations of sub-ranges and that language such as "between," "up to," "at least," "greater than," "less than," and the like include the number recited in the range and includes each individual member.

Unless otherwise defined, all technical and scientific terms used herein have the same meaning as commonly understood by one of ordinary skill in the art to which the present disclosure. In case of conflict, the present specification, including definitions, will control.

In addition, the materials, methods, and examples are illustrative only and not intended to be limiting. While various embodiments and suitable methodology and materials are described below, it will be understood that other suitable methodology and/or materials, which are similar to those described herein, may be employed to practice the compositions and methods of the present disclosure. The various embodiments, methodology, and materials disclosed herein are for purposes of illustration and are not intended to be limiting.

All references cited herein, whether supra or infra, including, but not limited to, patents, patent applications, and patent publications, whether U.S., PCT, or non-U.S. foreign, and all technical and/or scientific publications are hereby incorporated by reference in their entirety.

Platelet Lysates

The disclosure provides platelet lysate compositions in liquid or lyophilized form. The platelet lysate compositions are useful in a cell culture medium for culturing primary cells, such as endothelial cells. Platelet lysate compositions are also useful as wound healing compositions.

The platelet lysate (PL) can be a liquid fraction (or a powder derived from the lyophilization of such liquid fraction), which is produced by the lysis of platelets, including human platelets, and the separation of the liquid fraction from the solid fraction by, for example, filtration or centrifugation. Typically, it takes about 1 to about 2 liters of blood having a platelet count of 150,000/mm$^3$ to produce one unit of platelets having about $3 \times 10^{11}$ platelets. Any volume of a preparation containing platelets at the above concentrations can be used. For example, 30 ml, 50 ml, 100 ml, 500 ml, or an entire unit or combination of units of platelets can be used to obtain a platelet lysate and/or a plasma fraction. In embodiments, the PL contains the contents of from about $3 \times 10^8$ platelets per ml of PL to about $1 \times 10^9$ platelets per ml of PL, such as from about $4 \times 10^8$ platelets per 5 ml of PL, or from about $5 \times 10^8$ platelets per ml of PL, or from about $6 \times 10^8$ platelets per ml of PL, or from about $7 \times 10^8$ platelets per ml of PL, or from about $8 \times 10^8$ platelets per ml of PL, or from about $9 \times 10^8$ platelets per ml of PL to about $1 \times 10^9$ platelets per ml of PL or greater than $1 \times 10^9$ platelets per ml of PL.

The PL can be advantageously obtained from outdated platelet preparations (e.g., outdated platelet apheresis preparations or outdated large scale platelet isolation preparations). Outdated platelet preparations include, for example, platelet apheresis preparations and large scale platelet isolation preparations obtained from a live human and stored between 20° C. and 24° C. for more than about four days, or more than about five days, or more than about six days, or more than about seven days, or more than about eight days, 15 or more than about nine days, or more than about 10 days, or more than about 11, 12, 13, 14, or 15 days.

Platelets can be frozen and then thawed. This process can be repeated three or four times or more (but not required) and the supernatant that derives from the separation of insoluble components is collected, purified, and stored at −20° C. Methods for lysing which can be employed in methods for the preparation of the presently-disclosed cell culture media are described for example in U.S. Patent Publication No. 2011/0171731, which is herein incorporated by reference. The platelets can be collected and prepared for human use according to guidelines approved by Federal or International regulatory bodies.

In an embodiment, PL can be prepared from human apheresis platelet preparation derived from the blood of a human donor. As used herein, the term "apheresis" refers to an extracorporeal procedure in which whole blood from a donor or a patient is passed through an apparatus that separates platelets from the blood, and returns the remaining blood components to the donor's or patient's circulation. Apheresis platelet donors may fulfill, for example, the eligibility criteria defined by AABB Standards for Blood Banks and Transfusion Service and the Food and Drug Administration and screened using the Uniform Donor History Questionnaire (UDQ) and accompanying educational materials, as created by a coalition of regulatory, accrediting, and blood collecting institutions including the Food and Drug Administration, Centers for Disease Control and Prevention, Armed Services Blood Program, National Heart Lung and Blood Institute, American Blood Resources Association, AABB, American Red Cross, and America's Blood Centers.

In embodiments, apheresis platelet donors can be tested for one or more infectious diseases including, without limitation, syphilis, hepatitis C virus (HCV), hepatitis B virus, human immunodeficiency virus (HIV), human T-cell leukemia virus (HTLV), west Nile virus (WNV), and/or *T. cruzi* by employing FDA or international regulatory body approved methodologies readily available to those of skill in the art. In embodiments, the apheresis platelet preparations can be tested for bacterial contamination and/or endotoxin contamination according to FDA and/or international regulatory body guidelines. For example, an apheresis platelet preparation can be tested for bacterial contamination by inoculating anaerobic (e.g., Bactec Lytic/10 Anaerobic/F; Becton, Dickinson and Company; Sparks, MD) and aerobic culture bottles (e.g., Peds Bactec; Becton, Dickinson and Company; Sparks, MD) with platelet preparation samples, which culture bottles can be placed into a BacT/ALERT® system (bioMérieux, Durham, NC, USA) and monitored for CO2 generation whereby the absence of detectable CO2 production after 24 hours to 14 days confirms that the platelet preparation is free from bacterial contamination. In embodiments, an apheresis platelet preparation can be tested for endotoxin contamination by employing current FDA guidelines such as, for example, by inoculating a sterile endotoxin-free tube with a 1:50 dilution of a platelet lysate in Limulus Amebocyte Lysate (LAL) Reagent Water and running on an Endosafe Portable Test System (PTS; Charles River, Wilmington, MA), which utilizes LAL kinetic chromogenic methodology to measure color intensity directly related to the endotoxin concentration in a sample. Each disposable cartridge contains precise amounts of licensed LAL reagent, chromogenic substrate, and control standard endotoxin. The results obtained from each batch of PL preferably are <0.500 Endotoxin Units (EU)/mL.

In some embodiments, the PL can be prepared from a lysed platelet preparation comprising plasma. In such embodiments, the PL can include a plasma fraction and/or plasma components. In an embodiment, the PL is prepared from a lysed apheresis platelet preparation comprising plasma. Regardless of the source of the platelet preparation, such platelets can be lysed via one or more freeze/thaw cycles. Methods for preparing the PL generally include lysing a platelet preparation, such as an apheresis platelet preparation or a large-scale platelet isolation preparation, (b) centrifuging the lysate to obtain a supernatant, and (c) filtering the supernatant through a 0.45 m or smaller filter to obtain a filtrate, wherein the filtrate is the PL.

The platelet preparation can be lysed by a freeze/thaw cycle, which can be repeated by up to a total of two, three, four, five, or more total freeze/thaw cycles; by detergent lysis; by activation with thrombin, collagen, thromboxane A2, ADP or other factors; by manipulation of ionic strength; and/or by a combination of two or more such lysis methods, which thereby release the platelet contents.

Optionally, once lysed, the lysed platelets can be centrifuged at a force of from about 2000×g to about 5000×g, for from about 10 minutes to about 60 minutes to obtain a supernatant. Whether or not centrifugation is conducted, the supernatant or platelet lysate is collected and filtered through a filter having a pore size of about 0.45 m or less, about 0.2 m or less, or a sequential combination of filters first having a pore size of about 0.45 m or less and second having a pore size of about 0.2 m or less. The resulting filtrate can be used as a platelet lysate with or without further processing and/or can be combined with anti-coagulants, such as heparin. In embodiments, the platelet lysate does not substantially contain intact or un-lysed platelets and/or platelet debris.

In an embodiment, the platelet preparation is lysed by one or more freeze/thaw cycles. For example, a platelet preparation, including an apheresis platelet preparation, can be frozen at −70° C. or colder and maintained at −70° C. or colder for at least 24 hours prior to thawing the platelet preparations at room-temperature or under refrigeration. After thawing, the platelet preparations can be mixed and, optionally, returned to −70° C. or colder for a second and subsequent freeze-thaw cycles. Depending upon the precise cell culture media to be prepared, platelets can be lysed via two or more freeze/thaw cycles. The lysed platelet preparation can be further processed to remove un-lysed platelets, platelet debris, and/or platelet ghosts.

Optionally, lysed platelet preparations can be aseptically transferred to centrifuge tubes and centrifuged for from about 10 minutes to about 60 minutes at from about 1000×g to about 5000×g in, for example, a benchtop centrifuge (e.g., a Sorvall Legend T benchtop centrifuge). The resulting supernatants can be transferred to filters having a pore size of less than about 0.45 m (e.g., Pall Stericup, Catalog Number SCHV U05 RE; East Hills, NY or Nalgene Filter System, Catalog Number 167-0045; Rochester, NY) pre-fitted with one or more pre-filters (e.g., Glass Microfibre filters GF/B or GF/D; Whatman®, Florham Park, NJ), which is connected to a vacuum source or pumped through filters to permit product filtration. Alternatively, tangential flow filtration can be used to isolate and separate the components. Filtrates can, optionally, be pooled and filtered through a 0.2-micron filter unit (e.g., Pall Stericup, 25 Catalog Number SCHV U05 RE; East Hills, NY or Nalgene Filter System, Catalog Number 567-0020; Rochester, NY) pre-fitted with one or more pre-filters (e.g., Glass Microfibre filters GF/B or GF/D; Whatman®, Florham Park, NJ), which is connected to a vacuum source to permit product filtration.

Within certain aspects of these embodiments, the platelet lysate is prepared without washing of the platelets and/or platelet preparation prior to lysis, thereby retaining a plasma fraction that contains soluble plasma components, including one or more proteins, cytokines, and/or growth factors. In such embodiments, the platelet lysate can include both the contents of the lysed platelets as well as plasma or one or more plasma components.

Within related aspects, platelets can be maintained at a temperature of from about 2° C. to about 42° C., such as from about 2° C. to about 40° C., of from about 2° C. to about 38° C., of from about 2° C. to about 36° C., of from about 2° C. to about 30° C., of from about 5° C. to about 36° C., of from about 10° C. to about 36° C., of from about 15° C. to about 36° C., of from about 10 20° C. to about 30° C. for a period of about two, three, four, five, or more days in the presence of plasma prior to lysing the platelets. For example, a platelet preparation, such as an outdated platelet preparation obtained from an apheresis technique, can be lysed without prior removal of the plasma that is included within the platelet preparation. Once obtained, the lysed platelet preparation can be treated to remove unlysed platelets, platelet debris, and/or platelet ghosts. In embodiments, the platelet lysate does not substantially contain any intact or unlysed platelets. The supernatant and/or filtrate can then be obtained by centrifugation and/or by filtration, as described herein, and the resulting PL can be stored for later use or used without prior storage to prepare a cell culture media composition as disclosed herein.

Platelet lysates prepared as disclosed herein can be analyzed by standard proteomics methods, such as mass spectroscopy or ELISA, to determine the amount of growth factors, cytokines, and/or protein contained within the lysate. In embodiments, the concentrations of growth factors in the PL include from about 50 to about 225 pg/ml FGF-B, from about 1 to about 10 ng/ml EGF, from about 5 to about 30 ng/ml PDGF-BB, from about 50 to about 150 ng/ml IGF-1, from about 50 to about 175 ng/ml TGF-β, and/or from about 300 pg/ml to about 1100 pg/ml VEGF.

In an embodiment, the PL comprises from about 50 pg/ml FGF-B to about 75 pg/ml FGF-B, or to about 100 pg/ml FGF-B, or to about 150 pg/ml FGF-B, or to about 200 pg/ml FGF-B, or to about 225 pg/ml FGF-B.

In an embodiment, the PL comprises from about 1 ng/ml human EGF to about 2 ng/ml human EGF, or to about 5 ng/ml human EGF, or to about 10 ng/ml human EGF.

In an embodiment, the PL comprises from about 50 ng/ml human IGF-1 to 5 about 75 ng/ml human IGF-1, or to about 100 ng/ml human IGF-1, or to about 125 ng/ml human IGF-1, or to about 150 ng/ml human IGF-1.

In an embodiment, the PL comprises from about 5 ng/ml human PDGF-BB to about 10 ng/ml human PDGF-BB, or to about 20 ng/ml human PDGF-BB, or to about 25 ng/ml human PDGF-BB, or to about 30 ng/ml human PDGF-BB.

In an embodiment, the PL comprises from about 50 ng/ml human TGF-β to about 100 ng/ml human TGF-β, or to about 150 ng/ml human TGF-β, or to about 175 ng/ml human TGF-β.

In an embodiment, the PL comprises from about 300 pg/ml human VEGF to about 500 pg/ml human VEGF, or to about 750 pg/ml human VEGF, or to about 1000 pg/ml 15 human VEGF, or to about 1100 pg/ml human VEGF.

In an embodiment, concentrations of growth factors in platelet lysates prepared as described herein include from about 50 pg/ml FGF-B to about 100 pg/ml FGFB; from about 2 ng/ml EGF to about 7 ng/ml EGF; from about 75 ng/ml IGF-1 to about 125 ng/ml IGF-1; from about 5 ng/ml PDGF-BB to about 15 ng/ml PDGF-BB; from about 20 ng/ml TGF-β to about 150 ng/ml TGF-β; and/or from about 500 pg/ml VEGF to about 750 pg/ml VEGF. In some embodiments, the PL comprises about 500 pg to about 1100 pg of VEGF per mL. In an embodiment, the PL comprises about 500 to about 675 pg of VEGF per mL. In an embodiment, the PL comprises about 75 to about 225 pg of FGF-B per mL. In an embodiment, the PL comprises about 10 to about 14 ng of PDGF-BB per mL. In an embodiment, the PL comprises about 90 to about 150 ng of IGF-1 per mL. In an embodiment, the PL comprises about 100 to about 150 mg of TGF-β per mL. In some embodiments, the PL comprises a total protein concentration of at least about 30 mg per mL.

In an embodiment, the PL comprises from about 30 to about 100 mg of protein per mL. In another embodiment, the PL comprises from about 30 to about 75 mg of protein per mL. In another embodiment, the PL comprises from about 30 to about 50 mg protein per mL. In yet another embodiment, the PL comprises from about 40 to about 60 mg protein per mL.

In embodiments, the PL comprises a molecular weight fraction of 100 kDa or greater. In embodiments, the growth factor activity is substantially found in the higher molecular weight fraction of 100 kDa or greater. In embodiments, a PL without any substantially intact or unlysed platelets provides for growth of mesenchymal stem cells in vitro whereas washed intact or unlysed platelets with and without albumin do not support the growth of these cells. See FIG. 9.

Figure 7:
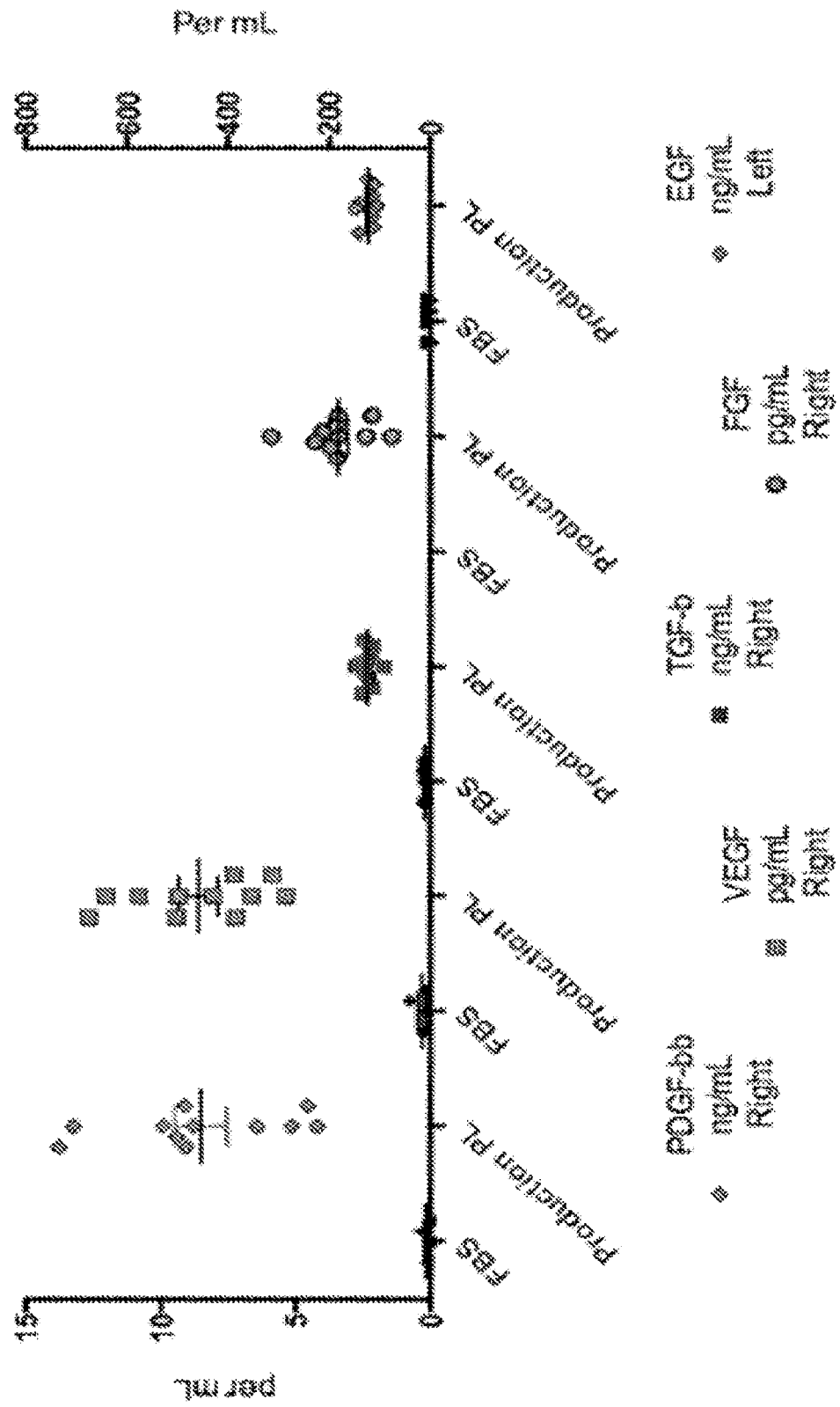
FIG. 7 is a graph showing typical amounts of EGF, FGF, PDGF-BB, TGF-β, and VEGF platelet lysates prepared according to the methodology described herein as compared to FBS.

The measured amounts of growth factors, cytokines, and/or protein can be compared to those measured in, for example, fetal bovine serum (FBS); human AB serum (HABS); a commercially available platelet lysate (e.g., Cryocheck; Catalog No. PNP-10; Precision BioLogic, Inc., Nova Scotia, Canada); and/or a fresh plasma without platelets. Average amounts of EGF, FGF, PDGF-BB, TGF-β, and VEGF within manufactured platelet lots according to the disclosure are shown in FIG. 7. The average amount of FGF-B within commercially available platelet lysates was about 80 pg/ml as compared to 180 pg/ml in platelet lysates prepared as disclosed herein. The average amount of PDGF-BB within commercially available platelet lysates was about 2.9 ng/ml as compared to 8.5 ng/ml in platelet lysates prepared as disclosed herein. The average amount of IGF-1 within commercially available platelet lysates was about 7.7 ng/ml as compared to 132 ng/ml in platelet lysates prepared as disclosed herein. The average amount of TGF-β within commercially available platelet lysates was about 37 ng/ml as compared to 54 ng/ml in platelet lysates prepared as disclosed herein.

Figure 8:
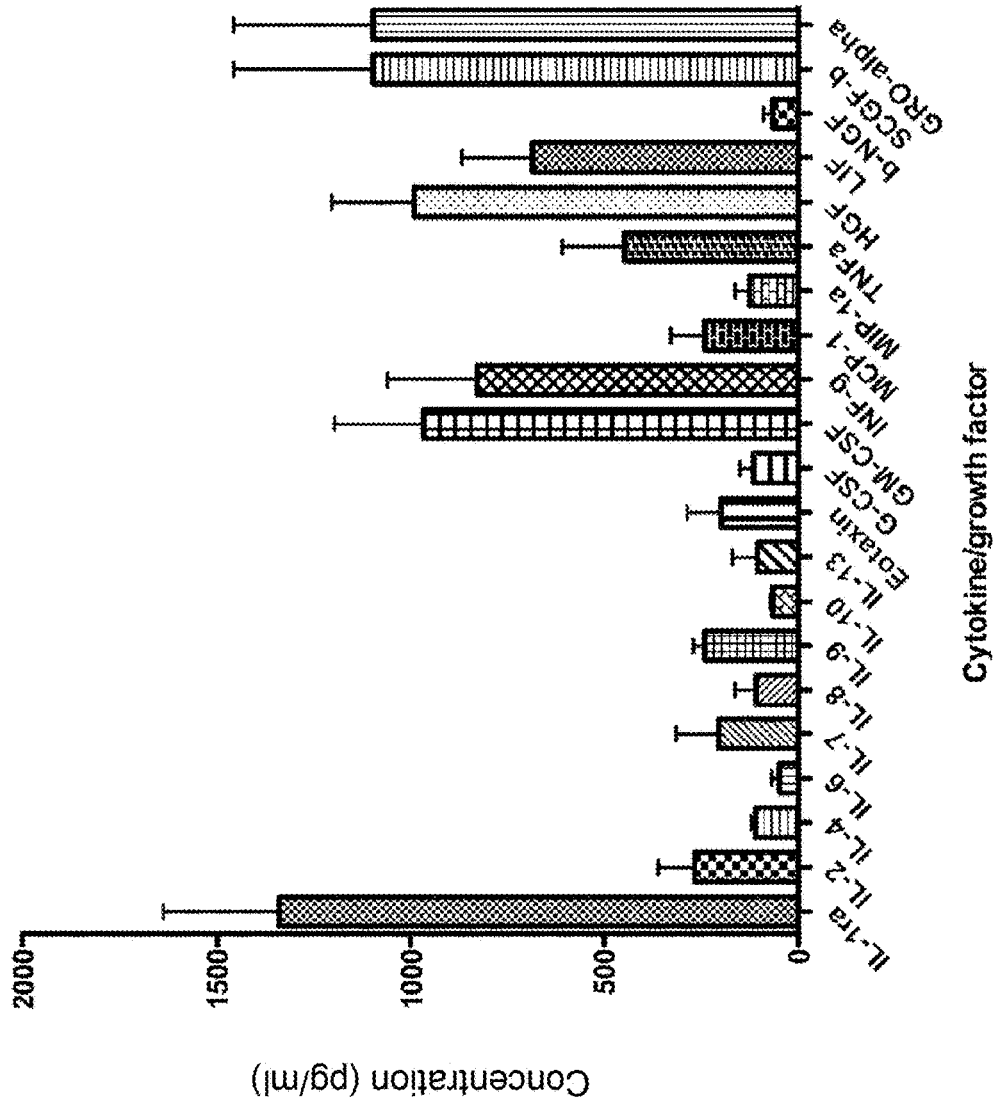
FIG. 8 is a graph showing typical amounts of 21 cytokines and growth factors in platelet lysates prepared according to the methodology described herein (using a BioPlex 26-plex assay; Biorad, 10 Hercules, CA).

Average amounts of 21 cytokines and other growth factors in platelet lysates prepared as described herein are presented in FIG. 8. The concentration range of cytokines and growth factors in FIG. 8 are shown in Table 1.

TABLE 1

| PL Component | Concentration (pg/ml) |
| --- | --- |
| IL-1Ra | 915-1925 |
| IL-2 | 85-405 |
| IL-4 | 90-150 |
| IL-6 | 25-85 |
| IL-7 | 1.5-380 |
| IL-8 | 20-210 |
| IL-9 | 185-295 |
| IL-10 | 55-71 |
| IL-12p70 | 78-1050 |
| IL-13 | 40-172 |
| GROa | 560-1790 |
| SCGF-b | 555-1799 |
| Eotaxin | 85-375 |
| G-CSF | 32-210 |

TABLE 1-continued

| PL Component | Concentration (pg/ml) |
|---|---|
| GM-CSF | 505-1225 |
| INF-g | 250-1350 |
| MCP-1 | 110-415 |
| MIP-1a | 55-195 |
| TNFa | 122-655 |
| HGF | 580-1320 |
| LIF | 305-1200 |
| b-NGF | 38-115 |

In some embodiments, the PL comprises one or more growth factor and/or cytokine selected from the group consisting of IL-1Ra, IL-2, IL-4, IL-6, IL-7, IL-8 IL-9, IL-10, IL-12p70, IL-13, GRO-alpha, SCGF-b, Eotaxin, G-CSF, GM-CSF, INF-gamma, MCP-1, MIP-1a, TNFa, HGF, LIF, b-PGF and combinations thereof. In one embodiment, the PL comprises from about 915 about to 1925 about pg IL-1Ra per ml. In one embodiment, the PL comprises from about 85 to about 405 pg IL-2 per ml. In one embodiment, the PL comprises from about 90 to about 150 pg IL-4 per ml. In one embodiment, the PL comprises from about 25 to about 85 pg IL-6 per ml. In one embodiment, the PL comprises from about 1.5 to about 380 pg IL-7 per ml. In one embodiment, the PL comprises from about 20 to about 210 pg IL-8 per 10 ml. In one embodiment, the PL comprises from about 185 to about 295 pg IL-9 per ml. In one embodiment, the PL comprises from about 55 to about 71 pg IL-10 per ml. In one embodiment, the PL comprises from about 78 to about 1050 pg IL-12p70 per ml. In one embodiment, the PL comprises from about 40 to about 172 pg IL-13 per ml. In one embodiment, the PL comprises from about 560 to about 1790 pg GRO-alpha (GROa) per 15 ml. In one embodiment, the PL comprises from about 555 to about 1799 pg SCGF-b per ml. In one embodiment, the PL comprises from about 85 to about 375 pg Eotaxin per ml. In one embodiment, the PL comprises from about 32 to about 210 pg G-CSF per ml. In one embodiment, the PL comprises from about 505 to about 1225 pg GM-CSF per ml. In one embodiment, the PL comprises from about 250 to about 1350 pg IFN-gamma (IFN-g) per 20 ml. In one embodiment, the PL comprises from about 110 to about 415 pg MCP-1 per ml. In one embodiment, the PL comprises from about 55 to about 195 pg MIP-1a per ml. In one embodiment, the PL comprises from about 122 to about 655 pg TNFa per ml. In one embodiment, the PL comprises from about 580 to about 1320 pg HGF per ml. In one embodiment, the PL comprises from about 305 to about 1200 pg LIF per ml. In one embodiment, the PL comprises from about 38 to about 115 pg b-PGF per ml.

In embodiments, a composition comprises a platelet lysate. In other embodiments, the composition further comprises an anticoagulant. In embodiments, the anticoagulant is selected from the group consisting of heparin, heparin derivatives, EDTA, citrate and oxalate. In embodiments, the composition includes an effective amount of anticoagulant to prevent formation of a clot. In embodiments, an anticoagulant is at least 2 units per ml.

In embodiments, a platelet lysate composition further comprises an exogenously added supplemental growth factor. Examples of suitable growth factors, include, but are not limited to basic fibroblast growth factor (FGF-B), epidermal growth factor (EGF), platelet-derived growth factor (PDGF), insulin-like growth factor (IGF), transforming growth factor (TGF), vascular endothelial growth factor (VEGF), liver growth factor (LGF), bone morphogenetic protein (BMP), colony stimulating factor (CSF), and combinations thereof.

In embodiments, for use with endothelial cell culture, the supplemental growth factor is FGF-B. In embodiments, for use with endothelial cell culture, the supplemental growth factor added is FGF-B of at least 1 ng/ml., or at least about 1 to 100 ng/ml, or 1 to 50 ng/ml., or 1 to 10 ng/ml. in addition to the amount of FGF-B present in the platelet lysate of about 0.050 to about 0.225 ng/ml FGF-B. In embodiments, the supplemental exogenous FGF-B added is at least about 1 to 2000 fold, 1 to 1000 fold, or 1 to 100 fold greater than that found in platelet lysate, per ng of FGF in the platelet lysate. In embodiments, the composition does not include other exogenously added growth factors, such as VEGF. In embodiments, the composition does not include fetal bovine serum.

In embodiments, for use with epithelial cell culture, the supplemental growth factor is EGF. In embodiments, for use with epithelial cell culture, the supplemental growth factor added is EGF of at least 1 ng/ml, or at least about 1 to 100 ng/ml, or 1 to 50 ng/ml., or 1 to 10 ng/ml. in addition to the amount of EGF present in the platelet lysate of. In embodiments, the supplemental exogenous EGF added is at least about 1 to 2000 fold, 1 to 1000 fold, or 1 to 100 fold greater than ng of EGF in the platelet lysate. In embodiments, another supplemental growth factor such as VEGF is not added to the platelet lysate or cell culture composition. In embodiments, the cell culture composition does not contain any fetal bovine serum or other animal serum.

In embodiments, for use with osteoblast cell culture, the supplemental growth factor is selected from the group consisting of IGF, TGF-β, BMP and combinations thereof. In embodiments, for use with osteoblast cell culture, the supplemental growth factor added is at least 1 ng/ml, or at least about 1 to 100 ng/ml, or 1 to 50 ng/ml., or 1 to 10 ng/ml. in addition to the amount of growth factor present in the platelet lysate. In embodiments, the supplemental exogenous growth factor(s) added is at least about 1 to 2000 fold, 1 to 1000 fold, or 1 to 100 fold greater than ng of growth factor in the platelet lysate. In embodiments, another supplemental growth factor such as VEGF is not added to the platelet lysate or cell culture composition. In embodiments, the cell culture composition does not contain any fetal bovine serum or other animal serum.

In embodiments, for use with melanocyte cell culture, the supplemental growth factor is selected from the group consisting of melanotropin, endothelin, TGFβ, and combinations thereof. In embodiments, for use with melanocyte cell culture, the supplemental growth factor added is at least 1 ng/ml, or at least about 1 to 100 ng/ml, or 1 to 50 ng/ml., or 1 to 10 ng/ml. in addition to the amount of growth factor present in the platelet lysate. In embodiments, the supplemental exogenous growth factor(s) is at least about 1 to 2000 fold, 1 to 1000 fold, or 1 to 100 fold greater than ng of growth factor(s) in the platelet lysate. In embodiments, another supplemental growth factor such as VEGF is not added to the platelet lysate or cell culture composition. In embodiments, the cell culture composition does not contain any fetal bovine serum or other animal serum.

In embodiments, the composition can further comprise an antioxidant and/or an immunosuppressant. In embodiments, the immunosuppressant is a steroid such as dexamethasone.

The PL or composition comprising PL can be lyophilized. Methods of lyophilization of peptide compositions are known to those of skill in the art and are described in Freeze-Drying/Lyophilization of Pharmaceutical and Biological Products", Marcel Dekker, Inc. New York, New York, eds. Rey, Louis and May, Joan C., 1999. Methods for lyophilizing PL are further described in Example 4.

In embodiments, a lyophilized composition comprises, consists essentially of or consists of a platelet lysate and a physiological acceptable carrier. In embodiments, the lyophilized composition does not include a bulking agents such as sucrose, mannitol, or trehalose. In embodiments, a physiological carrier has a pH of about 5.5-7.5 or about 6.5 to 7.5. In embodiments, the carrier is phosphate buffered saline or buffered cell culture media. In embodiments, as described above, a lyophilized composition can include a supplemental growth factor.

In embodiments, the lyophilized composition comprises a platelet lysate, at least one supplemental growth factor, and an anticoagulant. In embodiments, the platelet lysate contains at least 30 mg/ml protein. In embodiments, the supplemental growth factor is FGF and is present in the lyophilized composition in a ratio of at least 2000 to 1 or less of FGF in the platelet lysate. In embodiments, the lyophilized composition comprises 50% water, 40%, 30%, 20%, 10%, 5%, 2%, or 1% water or less.

In embodiments a wound healing composition comprises a lyophilized platelet lysate having 50% water, 40%, 30%, 20%, 10%, 5%, 2%, or 1% water or less, an aqueous solvent comprising at least 0.1 mM calcium, an anticoagulant, and a supplemental growth factor. In embodiments, the supplemental growth factor is FGF and is present in a ratio of at least 100 to 1 of FGF or less in the platelet lysate. In embodiments, the aqueous solvent contains about 0.1 to 100 mM calcium.

It was unexpectedly found that PL retains its growth enhancement properties after lyophilization. Although lyophilization is a useful technique for single recombinant proteins, the ability to lyophilize a complex protein mixture such as PL that retains its growth properties after lyophilization was unexpected and surprising. Desiccation is known to eliminate or reduce the infectiousness of viruses and some bacteria. Thus, lyophilization can be used to improve the safety profile of the PL. In addition, lyophilization can be used to improve the storage and transportation parameters of the PL, reducing the temperature required for storage and increasing the life span of proteins. In embodiments, the lyophilized platelet lysate composition has a storage stability of at least 6 months.

In embodiments, a platelet lysate composition whether in liquid or dried form can be coated onto a solid surface. Tissue culture vessels, cell culture vessels, scaffolds, and supports comprising a coating of PL are also disclosed. Vessels, supports, and scaffolds coated with the PL of the disclosure can support the growth of cells. For example, PL coated vessels, supports, and scaffolds can be used to culture EC and/or EPC in vitro.

The PL coating can be supplemented with one or more supplemental growth factors. These growth factors include, but are not limited to, fibroblast growth factor (FGF-B), epidermal growth factor (EGF), platelet derived growth factor (PDGF), insulin-like growth factor (IGF), transforming growth factor (TGF), vascular endothelial growth factor (VEGF), liver growth factor (LGF), bone morphogenetic protein (BMP), colony stimulating factor (CSF), hepatocyte growth factor (HGF), nerve growth factor (NGF), and combinations thereof. In some embodiments, the PL coating comprises an anticoagulant and/or about 0.1 mM to 100 mM calcium. In some embodiments, the vessels, supports, and/or scaffolds are treated with PL comprising a filtrate of a lysed human apheresis platelet preparation. In embodiments, the PL coating does not include fetal bovine serum.

In embodiments, a lyophilized composition is dried onto a solid substrate. In some cases, the solid substrate is a cell culture plate, a glass bead, a mesh, a wound covering, and a stent. In embodiments, the lyophilized composition is combined with a collagen or fibrin gel.

In embodiments, a basal medium can be added to a culture vessel coated with PL to form a cell culture medium composition in the culture vessel for culturing EC or EPC.

Cell Culture Media Compositions

The cell culture media compositions of the disclosure comprise one or more culture media, such as a basal medium or a restrictive basal medium, a platelet lysate (PL) or platelet lysate composition, such as a human platelet lysate (hPL), and, optionally, one or more additional supplemental growth factors. Examples of suitable growth factors, include, but are not limited to basic fibroblast growth factor (FGF-B), epidermal growth factor (EGF), platelet-derived growth factor (PDGF), insulin-like growth factor (IGF), transforming growth factor (TGF), vascular endothelial growth factor (VEGF), liver growth factor (LGF), bone morphogenetic protein (BMP), colony stimulating factor (CSF), and combinations thereof. For culture of EP or EPC for use in a human subject, the PL is preferably human PL.

In embodiments, a basal medium has a composition comprising essential amino acids, an energy source (e.g. a carbohydrate), vitamins including biotin, vitamin C and vitamin B12, salts such as sodium chloride, and sodium phosphate (e.g. in the form of phosphate buffered saline), and one or more nucleotides which supplies energy and building materials for cell growth and proliferation. In other embodiments, a basal medium comprises essential and nonessential amino acids, nucleobases, vitamins, glucose and other energy sources and inorganic salts. "Basal media" usually do not, however, contain growth factors or cytokines, or an animal serum. In embodiments, a basal medium is selected from the group consisting of DMEM, EGM, EBM, or MCDB.

The cell culture medium compositions generally include from about 50% to about 99% (v/v) of a basal medium. In an embodiment, the cell culture medium composition comprises about 60% to about 99% (v/v) of a basal medium. In another embodiment, the cell culture medium composition comprises about 70% to about 99% (v/v) of a basal medium. In another embodiment, the cell culture medium composition comprises about 80% to about 99% (v/v) of a basal medium. In another embodiment, the cell culture medium composition comprises about 85% to about 95% (v/v) of a basal medium. In another embodiment, the cell culture composition comprises about 85% to about 90% (v/v) of a basal medium. In another embodiment, the cell culture medium composition comprises about 90% to about 99% (v/v) of a basal medium. In another embodiment, the cell culture medium composition comprises about 90% to about 98% (v/v) of a basal medium. In yet another embodiment, the cell culture medium composition comprises about 95% to about 99% (v/v) of a basal medium. In some embodiments, the basal medium is a restrictive basal medium. In embodiments, the cell culture medium composition does not include fetal bovine serum.

Basal Medium

The basal media generally includes amino acids, vitamins, and inorganic salts. The amino acids can be essential and/or non-essential amino acids. Examples of essential amino acids include histidine, isoleucine, leucine, methionine, phenylalanine, lysine, threonine, tryptophan, and valine. Other amino acids include arginine, cysteine, glycine, glutamine, proline, tyrosine, alanine, asparagine, aspartic acid, glutamic acid, serine, and combinations thereof. In embodiments, the amino acids are selected from the group consisting of glycine at a concentration of from about 2 mg/L to about 20 mg/L, alanine at a concentration of from about 2 mg/L to about 6 mg/L, arginine at a concentration of from about 50 mg/L to about 180 mg/L, asparagine at a concentration of from about 6 mg/L to about 18 mg/L, aspartic acid at a concentration of from about 5 mg/L to about 15 mg/L, cysteine at a concentration of from about 27 mg/L to about 40 mg/L, glutamic acid at a concentration of from about 4 mg/L to about 8 mg/L, histidine at a concentration of from about 25 mg/L to about 45 mg/L, isoleucine at a concentration of from about 48 mg/L to about 72 mg/L, leucine at a concentration of from about 50 mg/L to about 140 mg/L, lysine at a concentration of from about 75 mg/L to about 210 mg/L, methionine at a concentration of from about 12 mg/L to about 21 mg/L, phenylalanine at a concentration of from about 30 mg/L to about 40 mg/L, proline at a concentration of from about 8 mg/L to about 21 mg/L, serine at a concentration of from about 22 mg/L to about 36 mg/L, threonine at a concentration of from about 8 mg/L to about 65 mg/L, tryptophan at a concentration of from about 3 mg/L to about 12 mg/L, tyrosine at a concentration of from about 15 mg/L to about 65 mg/L, valine at a concentration of from about 42 mg/L to about 130 mg/L and combinations thereof.

Examples of vitamins include, but are not limited to biotin, choline, pantothenate, folic acid, niacinamide, pyridoxal, riboflavin, thiamine, vitamin B12, i-Inositol, and combinations thereof. In embodiments, a cell culture composition comprises a vitamin selected from the group consisting of choline at a concentration of from about 7.5 mg/L to about 18 mg/L, pantothenate at a concentration of from about 1.8 mg/L to about 14 mg/L, folic acid at a concentration of from about 0.5 mg/L to about 3.0 mg/L, niacinamide at a concentration of from about 1.6 mg/L to about 7.2 mg/L, pyridoxal at a concentration of from about 1.0 mg/L to about 2.5 mg/L, riboflavin at a concentration of from about 0.003 to about 0.005 mg/L, thiamine at a concentration of from about 1.7 mg/L to about 4.0 mg/L, vitamin B12 at a concentration of from about 0.01 mg/L to about 0.02 mg/L, inositol at a concentration of from about 6 mg/L to about 15 mg/L and combinations thereof.

Examples of inorganic salts include but are not limited to, calcium chloride, cupric sulfate, ferric/ferrous sulfate, magnesium sulfate, potassium chloride, sodium bicarbonate, sodium chloride, sodium phosphate, zinc sulfate, ammonium metavanadate, ammonium molybdate, manganese sulfate, nickelous/nickel chloride, sodium selenite, sodium metasilicate, and combinations thereof.

The basal medium can further include antibiotics, nucleobases, such as thymidine, adenine, cytosine, and guanine, glucose, glycerol, and/or other energy sources, including for example fructose, galactose, mannose, sucrose, mannitol, and the like. In embodiments, a basal medium comprises components elected from the group consisting of glucose, linoleic acid, phenol red, putrescine, pyruvate, thymidine, adenine, and a combination thereof. In an embodiment, the basal medium comprises from about 200 to about 1600 mg/L amino acids, from about 20 to about 50 mg/L vitamins, from about 6000 to about 8000 mg/L inorganic salts, and from about 800 to about 3500 mg/L glucose.

Exemplary basal media compositions are shown in Table 2. Representative basal media that are commercially available include, for example, EBM™-2, a basal medium developed for culturing human EC and EPC in low serum conditions and is available from LonzaWalkersville, Inc. (Walkersville, MD); MCDB-131, a basal medium for culturing EC and is commercially available from different vendors such as, for example, MCDB-131 from Sigma (St. Louis, MO); and DMEM/F-12, a restrictive basal medium for supporting the growth of many different mammalian cells including, for example, MDCK, glial cells, fibroblasts, mesenchymal stromal cells, and human ECs.

TABLE 2

| | Concentration Range (mg/L) | | |
|---|---|---|---|
| | Formula A | MCDB-131 (Sigma) | DMEM/F-12 (LifeTech) |
| Amino Acids | | | |
| Glycine | 2-20 | 2.25 | 18.75 |
| Alanine | 2-6 | 2.67 | 4.45 |
| Arginine | 50-180 | 63.21 | 147.5 |
| Asparagine | 6-18 | 15.01 | 7.5 |
| Aspartic Acid | 5-15 | 13.31 | 6.65 |
| Cystine | 0-40 | | 31.29 |
| Cysteine | 0-45 | 35.12 | 17.56 |
| Glutamic Acid | 4-8 | 4.413 | 7.35 |
| Glutamine | 0-450 | 1.461 | 365.0 |
| Histidine | 25-45 | 41.92 | 31.48 |
| Isoleucine | 48-72 | 65.6 | 54.47 |
| Leucine | 50-140 | 131.2 | 59.05 |
| Lysine | 75-210 | 182.6 | 91.25 |
| Methionine | 12-21 | 14.92 | 17.24 |
| Phenylalanine | 30-40 | 33.04 | 35.48 |
| Proline | 8-21 | 11.51 | 17.25 |
| Serine | 22-36 | 31.53 | 26.25 |
| Threonine | 8-65 | 11.91 | 53.45 |
| Tryptophan | 3-12 | 4.08 | 9.02 |
| Tyrosine | 15-65 | 22.52 | 55.79 |
| Valine | 42-130 | 117.1 | 52.85 |
| Vitamins | | | |
| Biotin | $2.5 \times 10^{-03}$-$8.5 \times 10^{-03}$ | $7.329 \times 10^{-03}$ | $3.5 \times 10^{-03}$ |
| Choline | 7.5-18 | 13.96 | 8.98 |
| Pantothenate | 1.8-14 | 11.915 | 2.24 |
| Folic Acid | 0.5-3.0 | 0.5115 | 2.65 |
| Niacinamide | 1.6-7.2 | 6.105 | 2.02 |
| Pyridoxal | 1.0-2.5 | 2.056 | 2.013 |
| Riboflavin | 0.003-0.005 | 0.003764 | 0.219 |
| Thiamine | 1.7-4.0 | 3.373 | 2.17 |
| Vitamin B12 | 0.01-0.02 | 0.013554 | 0.68 |
| i-Inositol | 6-15 | 7.208 | 12.6 |
| Inorganic Salts | | | |
| Calcium Chloride | 90-270 | 177.5 | 116.6 |
| Cupric sulfate | 0.0010-0.0016 | 0.001249 | 0.0013 |
| Ferric/Ferrous sulfate | 0.24-0.48 | 0.278 | 0.417 |
| Magnesium Sulfate | 2000-3000 | 1,204 | 48.84 |
| Potassium Chloride | 250-350 | 298.2 | 311.8 |
| Sodium Chloride | 5500-7200 | 6,428 | 6,9995.5 |
| Sodium Phosphate | 60-150 | 71 | 133.52 |
| Zinc sulfate | $2 \times 10^{-04}$-$4 \times 10^{-04}$ | $2.88 \times 10^{-04}$ | 0.432 |
| Ammonium Metavanadate | $5 \times 10^{-04}$-$7 \times 10^{-04}$ | $5.85 \times 10^{-04}$ | |
| Ammonium Molybdate | 0.003-0.0045 | 0.003708 | |
| Manganese Sulfate | $1 \times 10^{-04}$-$3 \times 10^{-04}$ | $1.51 \times 10^{-04}$ | |

TABLE 2-continued

| | Concentration Range (mg/L) | | |
|---|---|---|---|
| | Formula A | MCDB-131 (Sigma) | DMEM/F-12 (LifeTech) |
| Nickelous/Nickel Chloride | $6 \times 10^{-05}$-$8 \times 10^{-05}$ | $7.1 \times 10^{-05}$ | |
| Sodium Selenite | 0.003-0.005 | 0.005187 | |
| Sodium Metasilicate | 2.2-3.5 | 2.842 | |
| Misc. Other | | | |
| Glucose | 800-3500 | 1,000 | 3151.0 |
| Linoleic Acid | 0-0.05 | | 0.042 |
| Phenol Red | 6-15 | 12.4 | 8.1 |
| Putrescine | $1 \times 10^{-04}$-$3 \times 10^{-04}$ | $1.61 \times 10^{-04}$ | 0.081 |
| Pyruvate | 45-130 | 110 | 55.0 |
| Thymidine | 0.02-0.03 | 0.02422 | 0.365 |
| Adenine | 0.1-0.2 | 0.1716 | |
| Thioctic Acid | $0$-$2.5 \times 10^{-03}$ | $2.063 \times 10^{-03}$ | |

Cell Culture Compositions Comprising Basal Medium and Platelet Lysate

Figure 2:
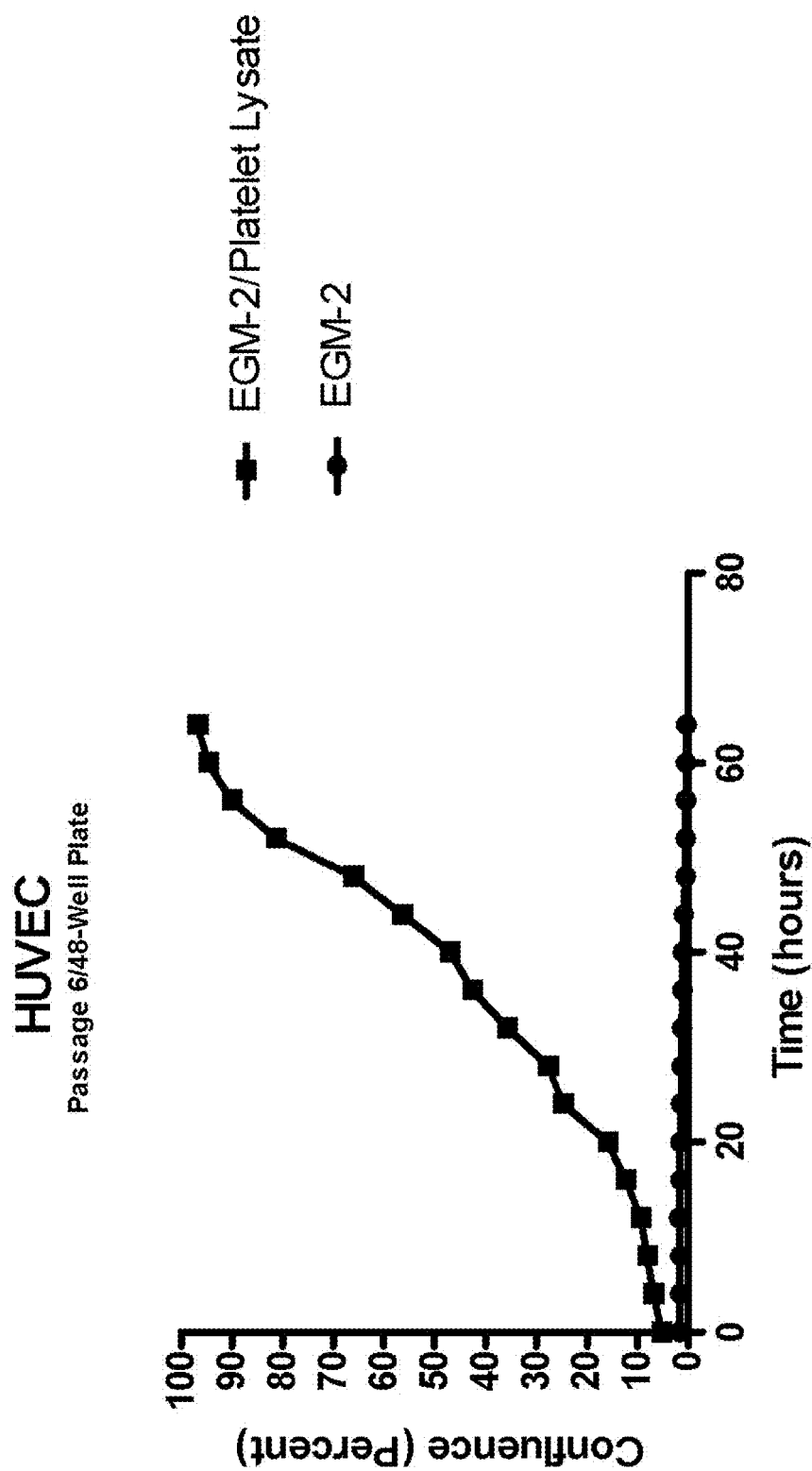
FIG. 2 is a graph of percent confluence as a function of time (from 0 to 64 hours) for human umbilical vein endothelial cells (HUVEC) plated onto 48-well plates containing EGM™-2 media supplemented with PL (■) or without any of the enclosed supplementation (EBM™-2 media 25 alone) (●), which demonstrates that, while EGM™-2 media alone does not support the growth of HUVECs, PL supplementation of EGM™-2 media is sufficient to achieve rapid growth of HUVECs in culture.
Figure 3:
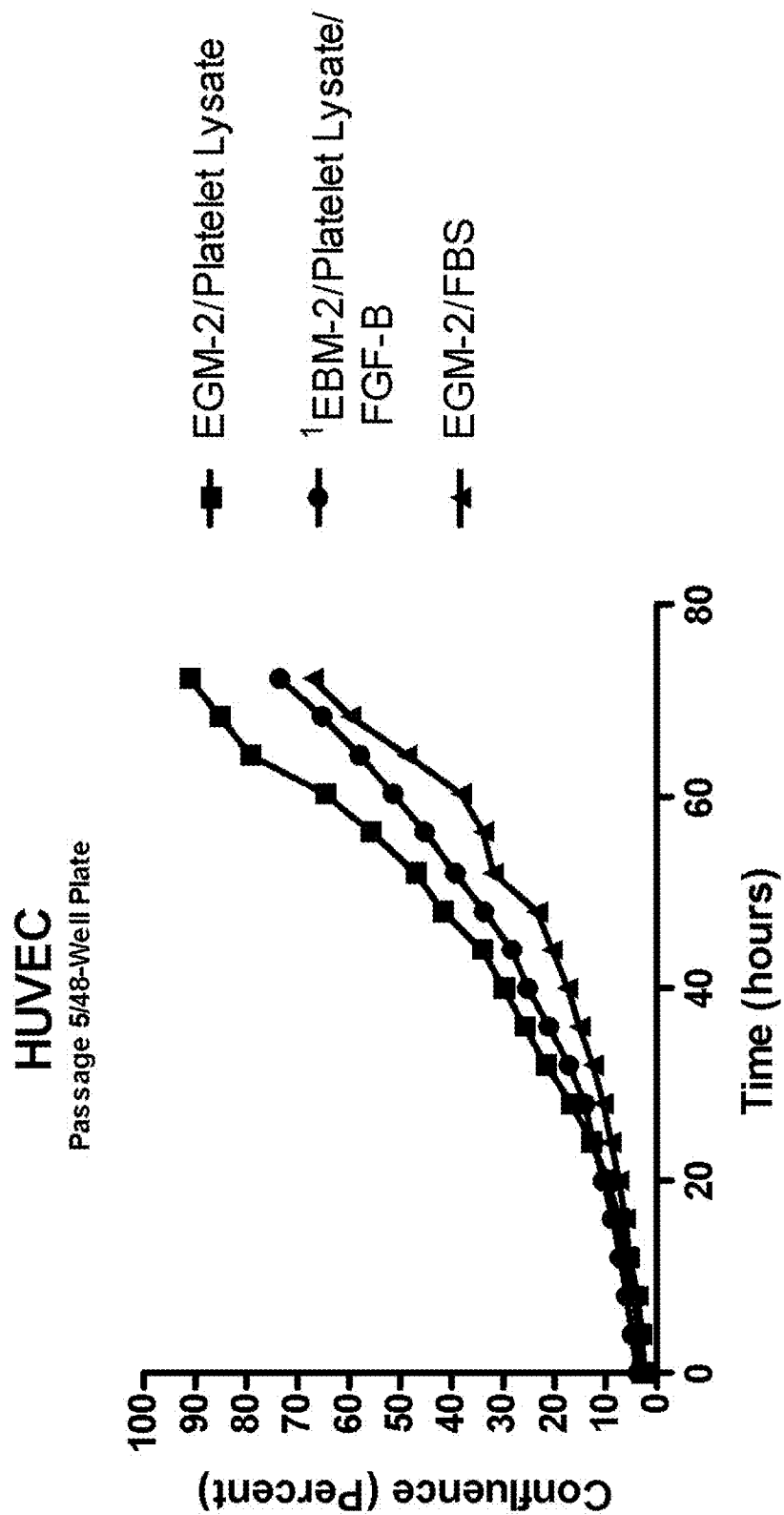
FIG. 3 is a graph of percent confluence as a function of time (from 0 to 72 hours) for human umbilical vein endothelial cells (HUVEC) plated onto 48-well plates containing EGM™-2 media supplemented with PL (■), EBM™-2 media supplemented with PL and FGF-B (●), and EGM™-2 media supplemented with FBS (▲), which demonstrates that HUVEC growth was comparable in EGM™-2 media supplemented with PL and EBM™-2 media supplemented with PL and FGF-B and that HUVEC growth in those two media was slightly more robust than was HUVEC growth in the traditional EGM™-2/FBS media.

In an embodiment, the PL or PL compositions can be used to replace animal serum, such as FBS, and/or to reduce or replace one or more cell culture medium supplements. For example, to form a complete cell culture medium, EGM™-2 media is supplemented with FBS and SingleQuots™, a mixture of cytokines, anti-oxidants, and anti-coagulant. In an embodiment, the FBS in EGM™-2 media is substituted with PL as described herein. As shown in FIG. 1, PL can be used to replace the FBS in EGM™-2 media for the culture of EC, such as HUVEC. In an embodiment, the FBS and SingleQuots™ in EGM™-2 media is substituted with PL as described herein. As shown in FIG. 2 and FIG. 3, PL can be used to replace the FBS and SingleQuots™ in EGM™-2 media for the culture of EC, such as HUVEC.

As disclosed herein, such PL or compositions thereof can be used in cell culture media compositions to obtain equivalent, or even superior, growth kinetics of endothelial cell cultures and/or endothelial progenitor cell cultures as compared to cultures using as basal medium that is supplemented with animal serum, such as FBS, or that is supplemented with one or more recombinant growth factor either in the presence or absence of a serum.

The cell culture media compositions of the present disclosure contain a sufficient amount of PL or compositions thereof for maintaining and/or growing mammalian endothelial cells and mammalian endothelial progenitor cells including, without limitation, endothelial cells and endothelial progenitor cells from humans, monkeys, horses, dogs, cats, rats, or mice, such as primary endothelial cells and primary endothelial progenitor cells from humans, monkeys, horses, dogs, cats, rats, or mice. Such cell culture media compositions may contain from about 1% to about 99% v/v of a PL according to the disclosure. For example, cell culture media compositions may contain from about 1 percent to about 2% v/v of a PL, or to about 5% v/v of a PL, or to about 8% v/v of a PL, or to about 10% v/v of a PL, or to about to 15% v/v of a PL, or to about 20% v/v of a PL, or to about 30% v/v of a PL, or to about 40% v/v of a PL, or to about 50% v/v of a PL, or to about 60% v/v of a PL, or to about 70% v/v of a PL, or to about 80% v/v of a PL, or to about 90% v/v of a PL, or to about 95% v/v of a PL.

In an embodiment, the cell culture medium composition contains from about 50% (v/v) of a basal cell culture medium, to about 60% (v/v) of a basal cell culture medium, to about 70% (v/v) of a basal cell culture medium, to about 80% (v/v) of a basal cell culture medium, to about 85% (v/v) of a basal cell culture medium, to about 90% (v/v) of a basal cell culture medium, to about 92% (v/v) of a basal cell culture medium, to about 98% (v/v) of a basal cell culture medium, to about 99% (v/v) of a basal cell culture medium, and from about 1% (v/v) to about 2% (v/v) of a PL, or to about 5% (v/v) of a PL, or to about 8% (v/v) of a PL, or to about 10% (v/v) of a PL, or to about 15% (v/v) of a PL, or to about 20% (v/v) of a PL, or to about 30% (v/v) of a PL, or to about 40% (v/v) of a PL, or to about 50% (v/v) of a PL, wherein the cell culture medium composition does not contain fetal bovine serum or other non-human mammalian serum.

In an embodiment, the cell culture medium composition comprises from about 50% (v/v) EBM™-2, to about 60% (v/v) EBM™-2, to about 70% (v/v) EBM™-2, to about 80% (v/v) EBM™-2, to about 90% (v/v) EBM™-2, to about 99% (v/v) EBM™-2 and from about 1% (v/v) to about 5% (v/v) of a PL, or to about 10% (v/v) of a PL, or to about 25% (v/v) of a PL, or to about 50% (v/v) of a PL, wherein the cell culture medium does not contain fetal bovine serum or other non-human mammalian serum.

In another embodiment, the cell culture medium composition comprises from about 50% (v/v) DMEM/F-12, to about 60% (v/v) DMEM/F-12, to about 70% 25 (v/v) DMEM/F-12, to about 80% (v/v) DMEM/F-12, to about 90% (v/v) DMEM/F-12, to about 99% (v/v) DMEM/F-12, and from about 1% (v/v) to about 5% (v/v) of a PL, or to about 10% (v/v) of a PL, or to about 25% (v/v) of a PL, or to about 50% (v/v) of a PL, wherein the cell culture medium does not contain fetal bovine serum or other non-human mammalian serum.

In yet another embodiment, the cell culture medium composition comprises from about 50% (v/v) MCDB-131, to about 60% (v/v) MCDB-131, to about 70% (v/v) MCDB-131, to about 80% (v/v) MCDB-131, to about 90% (v/v) MCDB-131, to about 99% (v/v) MCDB-131, and from about 1% (v/v) to about 5% (v/v) of a PL, or to about 10% (v/v) of a PL, or to about 25% (v/v) of a PL, or to about 50% (v/v) of a PL, wherein the cell culture medium does not contain fetal bovine serum or other non-human mammalian serum.

In embodiments, a cell culture medium composition comprising a basal medium, and platelet lysate is lyophilized, and has a water content comprising 50% water, 40%, 30%, 20%, 10%, 5%, 2%, or 1% water or less.

Additional Components of Cell Culture Medium

The cell culture medium composition can further be supplemented to include one or more exogenously added supplemental growth factors. In embodiments, no additional components are added to the cell culture medium composition if the platelet lysate composition includes those components. In embodiments, when the supplemental growth factor and/or anti-coagulant is added to a platelet lysate composition, no further additional supplemental growth factor and/or anti-coagulant is added to the cell culture composition.

In an embodiment, the growth factor comprises FGF, EGF, HGF, NGF, PDGF, IGF, TGF, VEGF, LGF, or a combination thereof. In embodiments, the cell culture composition includes an anti-coagulant, such as heparin, heparin derivatives, EDTA, citrate and oxalate.

In an embodiment, the amount of exogenous growth factor added to the cell culture medium composition is from about 0.5 log to about 0.75 log, from about 0.5 log to about 1 log, from about 0.5 log to about 1.5 log, from about 0.5 log to about 2 log, from about 0.5 log to about 2.5 log, or from about 0.5 log to about 3 log the amount of the growth factor per ml present in the PL before supplementation. In another embodiment, the amount of exogenous growth factor added to the cell culture medium composition is from about 0.75 log to about 1 log, from about 0.75 log to about 1.5 log, from about 0.75 log to about 2 log, from about 0.75 log to about 2.5 log, or from about 0.75 log to about 3 log the amount of the growth factor per ml present in the PL before supplementation. In another embodiment, the amount of exogenous growth factor added to the cell culture medium composition is from about 1 log 20 to about 1.5 log, from about 1 log to about 2 log, from about 1 log to about 2.5 log, or from about 1 log to about 3 log the amount of the growth factor per ml present in the PL before supplementation. In yet embodiment, the amount of exogenous growth factor added to the cell culture medium composition is from about 1.5 log to about 2 log, from about 1.5 log to about 2.5 log, or from about 1.5 log to about 3 log the amount of the growth factor per ml present in the PL before supplementation.

In an embodiment, the cell culture medium composition is supplemented with FGF-B at a concentration of from about 50 pg/ml to about 225 ng/ml of the medium. In another embodiment, the cell culture medium composition is supplemented with EGF at a concentration of from about 1 to about 1000 ng/ml of the medium. In another embodiment, the cell culture medium composition is supplemented with PDGF-BB at a concentration of from about 5 to about 3000 ng/ml of the medium. In another embodiment, the cell culture medium composition is supplemented with IGF-1 at a concentration of from about 50 to about 15000 ng/ml of the medium. In another embodiment, the cell culture medium composition is supplemented with TGF-β at a concentration of from about 50 to about 17500 ng/ml of the medium. In yet another embodiment, the cell culture medium composition is supplemented with VEGF at a concentration of from about 0.3 to about 110 ng/ml of the medium. In yet another embodiment, the cell culture medium composition is supplemented with LGF at a concentration of from about 0.5 to about 500 ng/ml of the medium. In yet another embodiment, the cell culture medium composition is supplemented 10 with hepatocyte growth factor (HGF) at a concentration of from about 0.5 to about 15 ng/ml of the medium. In yet another embodiment, the cell culture medium composition is supplemented with nerve growth factor (NGF) at a concentration of from about 0.1 to about 20 ng/ml of the medium.

In embodiments, for use with epithelial cell culture, the supplemental growth factor is EGF. In embodiments, for use with epithelial cell culture, the supplemental growth factor added is EGF of at least 1 ng/ml, or at least about 1 to 100 ng/ml, or 1 to 50 ng/ml., or 1 to 10 ng/ml. in addition to the amount of EGF present in the platelet lysate of. In embodiments, the supplemental exogenous EGF added is at least about 1 to 2000 fold, 1 to 1000 fold, or 1 to 100 fold greater than ng of EGF in the platelet lysate. In embodiments, another supplemental growth factor such as VEGF is not added to the platelet lysate or cell culture composition. In embodiments, the cell culture composition does not contain any fetal bovine serum or other animal serum.

In embodiments, for use with osteoblast cell culture, the supplemental growth factor is selected from the group consisting of IGF, TGF-β, BMP and combinations thereof. In embodiments, for use with osteoblast cell culture, the supplemental growth factor added is at least 1 ng/ml, or at least about 1 to 100 ng/ml, or 1 to 50 ng/ml., or 1 to 10 ng/ml. in addition to the amount of growth factor present in the platelet lysate. In embodiments, the supplemental exogenous growth factor(s) added is at least about 1 to 2000 fold, 1 to 1000 fold, or 1 to 100 fold greater than ng of growth factor in the platelet lysate. In embodiments, another supplemental growth factor such as VEGF is not added to the platelet lysate or cell culture composition. In embodiments, the cell culture composition does not contain any fetal bovine serum or other animal serum.

In embodiments, for use with melanocyte cell culture, the supplemental growth factor is selected from the group consisting of melanotropin, endothelin, TGFβ, and combinations thereof. In embodiments, for use with melanocyte cell culture, the supplemental growth factor added is at least 1 ng/ml, or at least about 1 to 100 ng/ml, or 1 to 50 ng/ml., or 1 to 10 ng/ml. in addition to the amount of growth factor present in the platelet lysate. In embodiments, the supplemental exogenous growth factor(s) is at least about 1 to 2000 fold, 1 to 1000 fold, or 1 to 100 fold greater than ng of growth factor(s) in the platelet lysate. In embodiments, another supplemental growth factor such as VEGF is not added to the platelet lysate or cell culture composition. In embodiments, the cell culture composition does not contain any fetal bovine serum or other animal serum In an embodiment, the cell culture medium composition comprises from 15 about 50% (v/v) of a basal cell culture medium, to about 60% (v/v) of a basal cell culture medium, to about 70% (v/v) of a basal cell culture medium, to about 85% (v/v) of a basal cell culture medium, to about 90% (v/v) of a basal cell culture medium, to about 92% (v/v) of a basal cell culture medium, to about 95% (v/v) of a basal cell culture medium, to about 98% (v/v) of a basal cell culture medium, to about 99% (v/v) of a basal cell culture medium; 20 from about 1% (v/v) to about 2% (v/v) of a PL, or to about 5% (v/v) of a PL, or to about 10% (v/v) of a PL, or to about 15% (v/v) of a PL, or to about 30% (v/v) of a PL, or to about 40% (v/v) of a PL, or to about 50% (v/v) of a PL; and from about from about 50 to 100 pg/ml, or from about 100 pg/ml to about 1 ng/ml, or from about 1 to about 10 ng/ml, from about 5 to about 22.5 ng/ml, from about 22.5 to about 225 ng/ml of exogenously added FGF. In an embodiment, the basal medium comprises EBM™-2 MCDB-131, or DMEM/F-12. In embodiments, the cell culture medium does not include exogenously added VEGF. Preferably, the cell culture medium composition does not contain fetal bovine serum or other non-human mammalian serum.

In another embodiment, the cell culture medium composition comprises from about 50% (v/v) of a basal cell culture medium, to about 60% (v/v) of a basal cell culture medium, to about 70% (v/v) of a basal cell culture medium, to about 85% (v/v) of a basal cell culture medium, to about 90% (v/v) of a basal cell culture medium, to about 92% (v/v) of a basal cell culture medium, to about 95% (v/v) of a basal cell culture medium, to about 98% (v/v) of a basal cell culture medium, to about 99% (v/v) of a basal cell culture medium; from about 1% (v/v) to about 2% (v/v) of a PL, or to about 5% (v/v) of a PL, or to about 10% (v/v) of a PL, or to about 15% (v/v) of a PL, or to about 30% (v/v) of a PL, or to about 40% (v/v) of a PL, or to about 50% (v/v) of a PL; and from about 1 to about 10 ng/ml, or from about 10 to about 20 ng/ml, from about 20 to about 50 ng/ml, from about 50 to about 100 ng/ml, or from about 100 to about 1000 ng/ml of exogenously added EGF. In embodiments, the cell culture medium does not include exogenously added VEGF. In an embodiment, the basal medium comprises EBM™-2, MCDB-131, or DMEM/F-12. Preferably, the cell culture medium composition does not contain fetal bovine serum or other non-human mammalian serum In another embodiment, the cell culture medium composition comprises from about 50% (v/v) of a basal cell culture medium, to about 60% (v/v) of a basal cell culture medium, to about 70% (v/v) of a basal cell culture medium, to about 85% (v/v) of a basal cell culture medium, to about 90% (v/v) of a basal cell culture medium, to about 92% (v/v) of a basal cell culture medium, to about 95% (v/v) of a basal cell culture medium, to about 98% (v/v) of a basal cell culture medium, to about 99% (v/v) of a basal cell culture medium; from about 1% (v/v) to about 2% (v/v) of a PL, or to about 5% (v/v) of a PL, or to about 10% (v/v) of a PL, or to about 15% (v/v) of a PL, or to about 30% (v/v) of a PL, or to about 20 40% (v/v) of a PL, or to about 50% (v/v) of a PL; and from about 5 to about 50 ng/ml, from about 50 to about 100 ng/ml, from about 100 to about 200 ng/ml, from about 200 to about 300 ng/ml, or from about 300 to about 3000 ng/ml of exogenously added PDGF-BB. In embodiments, the cell culture medium does not include exogenously added VEGF. In an embodiment, the basal medium comprises EBMT-2, MCDB-131, or DMEM/F-12. Preferably, the cell culture medium composition does not contain fetal bovine serum or other non-human mammalian serum.

In another embodiment, the cell culture medium composition comprises from about 50% (v/v) of a basal cell culture medium, to about 60% (v/v) of a basal cell culture medium, to about 70% (v/v) of a basal cell culture medium, to about 85% (v/v) of a basal cell culture medium, to about 90% (v/v) of a basal cell culture medium, to about 92% (v/v) of a basal cell culture medium, to about 95% (v/v) of a basal cell culture medium, to about 98% (v/v) of a basal cell culture medium, to about 99% (v/v) of a basal cell culture medium; from about 1% (v/v) to about 2% (v/v) of a PL, or to about 5% (v/v) of a PL, or to about 10% (v/v) of a PL, or to about 15% (v/v) of a PL, or to about 30% (v/v) of a PL, or to about 40% (v/v) of a PL, or to about 50% (v/v) of a PL; and from about 50 to about 100 ng/ml, 5 from about 100 to about 200 ng/ml, from about 200 to about 500 ng/ml, from about 500 to about 1000 ng/ml, from about 1000 to about 1500 ng/ml, or from about 1500 to about 15000 ng/ml of exogenously added IGF-1. In embodiments, the cell culture medium does not include exogenously added VEGF. In an embodiment, the basal medium comprises EBM™-2, MCDB-131, or DMEM/F-12. Preferably, the cell culture medium composition does not contain fetal bovine serum or other non-human mammalian serum.

In another embodiment, the cell culture medium composition comprises from about 50% (v/v) of a basal cell culture medium, to about 60% (v/v) of a basal cell culture medium, to about 70% (v/v) of a basal cell culture medium, to about 80% (v/v) of a basal cell culture medium, to about 85% (v/v) of a basal cell culture medium, to about 90% (v/v) of a basal cell culture medium, to about 92% (v/v) of a basal cell culture medium, to about 95% (v/v) of a basal cell culture medium, to about 98% (v/v) of a basal cell culture medium, to about 99% (v/v) of a basal cell culture medium; from about 1% (v/v) to about 2% (v/v) of a PL, or to about 5% (v/v) of a PL, or to about 10% (v/v) of a PL, or to about 15% (v/v) of a PL, or to about 30% (v/v) of a PL, or to about 40% (v/v) of a PL, or to about 50% (v/v) of a PL; and from about 50 to about 100 ng/ml, from about 100 to about 200 ng/ml, from about 200 to about 500 ng/ml, from about 500 to about 1000 ng/ml, from about 1000 to about 1750 ng/ml, or from about 1750 to about 17500 ng/ml of exogenously added TGF-β. In embodiments, the cell culture medium does not include exogenously added VEGF. In an embodiment, the basal medium comprises EBMT-2, MCDB-131, or DMEM/ F-12. Preferably, the cell culture medium composition does not contain fetal bovine serum or other non-human mammalian serum.

In another embodiment, the cell culture medium composition comprises from about 50% (v/v) of a basal cell culture medium, to about 60% (v/v) of a basal cell culture medium, to about 70% (v/v) of a basal cell culture medium, to about 80% (v/v) of a basal cell culture medium, to about 85% (v/v) of a basal cell culture medium, to about 90% (v/v) of a basal cell culture medium, to about 92% (v/v) of a basal cell culture medium, to about 95% (v/v) of a basal cell culture medium, to about 98% (v/v) of a basal cell culture medium, to about 99% (v/v) of a basal cell culture medium; from about 1% (v/v) to about 2% (v/v) of a PL, or to about 5% (v/v) of a PL, or to about 10% (v/v) of a PL, or to about 15% (v/v) of a PL, or to about 30% (v/v) of a PL, or to about 40% (v/v) of a PL, or to about 50% (v/v) of a PL; and from about 0.3 to about 1 ng/ml, from about 1 to about 4 ng/ml, from 5 about 4 to about 8 ng/ml, from about 8 to about 11 ng/ml, or from about 11 to about 110 ng/ml of exogenously added VEGF. In an embodiment, the basal medium comprises EBM™-2, MCDB-131, or DMEM/F-12. Preferably, the cell culture medium composition does not contain fetal bovine serum or other non-human mammalian serum In another embodiment, the cell culture medium composition comprises from 10 to about 50% (v/v) of a basal cell culture medium, to about 60% (v/v) of a basal cell culture medium, to about 70% (v/v) of a basal cell culture medium, to about 80% (v/v) of a basal cell culture medium, to about 85% (v/v) of a basal cell culture medium, to about 90% (v/v) of a basal cell culture medium, to about 92% (v/v) of a basal cell culture medium, to about 95% (v/v) of a basal cell culture medium, to about 98% (v/v) of a basal cell culture medium, to about 99% (v/v) of a basal cell culture medium; from about 1% (v/v) to about 2% (v/v) of a PL, or to about 5% (v/v) of a PL, or to about 10% (v/v) of a PL, or to about 15% (v/v) of a PL, or to about 30% (v/v) of a PL, or to about 40% (v/v) of a PL, or to about 50% (v/v) of a PL; and from about 0.5 to about 1 ng/ml, from about 1 to about 5 ng/ml, from about 5 to about 20 ng/ml, from about 20 to about 50 ng/ml, or from about 50 to about 500 20 ng/ml of exogenously added LGF. In embodiments, the cell culture medium does not include exogenously added VEGF. In an embodiment, the basal medium comprises EBM™-2, MCDB-131, or DMEM/F-12. Preferably, the cell culture medium composition does not contain fetal bovine serum or other non-human mammalian serum.

In another embodiment, the cell culture medium composition comprises from about 50% (v/v) of a basal cell culture medium, to about 60% (v/v) of a basal cell culture medium, to about 70% (v/v) of a basal cell culture medium, to about 80% (v/v) of a basal cell culture medium, to about 85% (v/v) of a basal cell culture medium, to about 90% (v/v) of a basal cell culture medium, to about 92% (v/v) of a basal cell culture medium, to about 95% (v/v) of a basal cell culture medium, to about 98% (v/v) of a basal cell culture medium, to about 99% (v/v) of a basal cell culture medium; from about 1% (v/v) to about 2% (v/v) of a PL, or to about 5% (v/v) of a PL, or to about 10% (v/v) of a PL, or to about 15% (v/v) of a PL, or to about 30% (v/v) of a PL, or to about 40% (v/v) of a PL, or to about 50% (v/v) of a PL; and from about 0.5 to about 1 ng/ml, from about 1 to about 5 ng/ml, from about 5 to about 10 ng/ml, from about 10 to about 15 ng/ml, or from about 0.5 to about 15 ng/ml of exogenously added HGF. In embodiments, the cell culture medium does not include exogenously added VEGF. In an embodiment, the basal medium comprises EBM™-5 2, MCDB-131, or DMEM/F-12. Preferably, the cell culture medium composition does not contain fetal bovine serum or other non-human mammalian serum.

In yet another embodiment, the cell culture medium composition comprises from about 50% (v/v) of a basal cell culture medium, to about 60% (v/v) of a basal cell culture medium, to about 70% (v/v) of a basal cell culture medium, to about 80% (v/v) of a basal cell culture medium, to about 85% (v/v) of a basal cell culture medium, to about 90% (v/v) of a basal cell culture medium, to about 92% (v/v) of a basal cell culture medium, to about 95% (v/v) of a basal cell culture medium, to about 98% (v/v) of a basal cell culture medium, to about 99% (v/v) of a basal cell culture medium; from about 1% (v/v) to about 2% (v/v) of a PL, or to about 5% (v/v) of a PL, or to about 10% (v/v) of a PL, or to about 15% (v/v) of a PL, or to about 30% (v/v) of a PL, or to about 40% (v/v) of a PL, or to about 50% (v/v) of a PL; and from about 0.1 to about 1 ng/ml, from about 1 to about 5 ng/ml, from about 5 to about 10 ng/ml, or from about 10 to about 20 ng/ml of exogenously added NGF. In embodiments, the cell culture medium does not include exogenously added VEGF. In an embodiment, the basal medium comprises EBMT-2, MCDB-131, or DMEM/F-12. Preferably, the cell culture medium composition does not contain fetal bovine serum or other non-human mammalian serum.

Solid Substrates

Another aspect of the disclosure is a solid substrate coated with a human platelet lysate or composition thereof. In embodiments, the solid substrate is a tissue or cell culture vessels, such culture plates, flasks, dishes, and/or wells for culturing a cell or tissue, including a human cell, such as a human endothelial cell or a human endothelial progenitor cell, in particular a primary human endothelial cell or a primary human endothelial progenitor cell in culture. The cell culture vessels can be used in combination with a culture medium, such as a basal medium, to permit the attachment, maintenance, and/or growth of a cell, such as an endothelial cell or an endothelial progenitor cell for use in research and/or in a clinical setting.

In other embodiments, a solid substrate includes a bead, a stent, a wound covering, and a syringe. In yet other embodiments, the platelet lysate or compositions thereof can be combined with a scaffold, fibrin, or collagen gel.

The culture vessels are coated with a PL composition as described herein or a PL composition supplemented with human growth factors as described herein using conventional methods. For example, a sterilized culture vessel, such as 6-well cell culture plate, can be pretreated with a human PL according to the disclosure supplemented with a growth factor as described herein, such as FGF, and then air-dried to form the coating. The coated culture vessel can be used directly to seed cells or can be stored at –20 C for later use. Alternatively, the culture vessel can be electrostatically or spray coated with a lyophilized form of the PL or composition thereof.

The PL coating can optionally be combined with coating of extracellular matrix proteins. As endothelial cells are adherent cells that attach to the inner surface of cell culture vessels, inclusion of extracellular matrix proteins in the coating promote adherence of EC cells to culture vessels. Common extracellular matrix proteins useful for coating cell culture vessels for EC include but are not limited to collagen I, collagen IV, fibronectin, gelatin, laminin. Synthetic compounds, such as matrigel matrix and poly-lysine, can be included as an alternative to extracellular matrix protein for coating purposes.

Basal media can be added to the coated culture vessel to form a cell culture medium composition in the culture vessel for culturing primary cells such as EC or EPC. The EC or EPC are then plated in the culture vessel and cultured under conditions that promote the growth and/or maintenance of EC or EPC using conventional cell and tissue culture techniques. The release of PL components and/or the supplemented growth factor from the coating can be monitored if desired by incorporating radio or stable isotope labeled to the bulk of unlabeled PL and/or growth factor. The bioactivity of PL and/or the supplemented growth factor in the coating can be evaluated, for example, by cell proliferation assay.

The PL coating can optionally be combined with a coating of extracellular matrix proteins as described herein. The scaffold can be coated with PL to promote, for example, vascularization of the scaffold. Native (e.g., decellularized human tissues or organs) or fabricated (e.g., polymers) scaffolds are also disclosed. Scaffolds coated with PL or a PL supplemented with human growth factors as described herein are also disclosed. The scaffolds include but are not limited to native scaffolds, such as decellularized human tissues or organs, fabricated extracellular matrices, and polymer scaffolds. The scaffolds can be biodegradable. One or more surfaces of the scaffolds can be coated with PL or a PL compositions supplemented with human growth factors as described herein. For example, to improve angiogenesis, a porous polymer scaffold can be coated with a PL supplemented with human growth factor(s) as described herein. The coated scaffold can either be directly implanted in vivo or cultured with ECs or EPCs for additional tissue engineering before being implanted.

Within related aspects, the platelet lysate and or one or more cytokine or other growth factor can be concentrated or lyophilized prior to coating on the scaffold. The scaffolds disclosed herein can be used in combination with a culture medium, such as a basal culture medium, to permit the attachment and growth of a cell, such as an endothelial cell or an endothelial progenitor cell, thereby facilitating, for example, the formation of a tissue engineered blood vessel for use in research or for use clinically as a tissue graft, which is employed during a surgical procedure.

In embodiments, the platelet lysate composition or cell culture composition can be coated onto a solid substrate such as a bead, a mesh, a wound covering, and a stent. The platelet lysate composition or cell culture composition can be coated as a liquid and air dried or lyophilized and spray coated.

Methods for Preparing and Using Cell Culture Media Compositions

Within other embodiments, the present disclosure provides methods for making cell culture media compositions, the methods including the steps of selecting one or more culture media, such as a basal medium or a restrictive basal medium; adding a platelet lysate (PL) or composition thereof, such as a human platelet lysate, to the one or more culture media; and, optionally, adding one or more exogenous growth factors as described herein to the media, including for example FGF-B, EGF, PDGF, IGF, TGF, VEGF, LGF, HGF, NGF and combinations thereof.

The present disclosure also provides methods for maintaining and/or growing a cell, including a human cell, such as a human endothelial cell or a human endothelial progenitor cell, human epithelial cell, human osteoblast, and human melanocyte. The methods including the step of plating, culturing, or seeding such a cell in a cell culture media composition, which contains one or more culture media, such as a basal medium or a restrictive basal medium, platelet lysate (PL), such as human platelet lysate (hPL), and, optionally, one or more additional factors including, for example, one or more cytokines such as one or more of basic FGF-B, EGF, PDGF, IGF, TGF, VEGF, HGF, NGF and/or LGF. In embodiments, for endothelial cells a single supplemental growth factor is added, and other supplemental growth factors such VEGF are not added to the cell culture medium. In embodiments, the cell culture medium does not contain fetal bovine serum.

In embodiments a method comprises providing a cell culture vessel coated with a lyophilized composition comprising platelet lysate and a supplemental growth factor as described herein, adding basal medium to the cell culture vessel, adding primary cells and incubating the cells under conditions to reach at least 80% confluence. In embodiments, no fetal bovine serum is added.

The plated cells, such as ECs or EPCs, are then cultured under conditions that promote the growth and/or maintenance of the cells using conventional cell and tissue culture techniques. In an embodiment, said cells are at least 80% confluent within about 60 hours to about 100 hours of culture time. In embodiments, the cell culture media compositions of the present disclosure do not include a non-human serum, such as a fetal bovine serum. These cell culture media compositions can be used to maintain and/or grow mammalian cells and mammalian progenitor cells, in particular human endothelial cells and human endothelial progenitor cells, such as primary human endothelial cells and primary human endothelial progenitor cells under GMP conditions, which permit clinicians or other medical personnel to employ such endothelial cells in therapeutic modalities for the treatment of diseases that are susceptible to the in vivo administration of such endothelial cells or endothelial progenitor cells and/or the in vivo administration of one or more product or material that is cultured in or generated with such endothelial cells or endothelial progenitor cells.

In embodiments, methods of the disclosure include a method of treating a condition by administering endothelial cells cultured in vitro to a subject in need thereof. The PL or compositions thereof can also be autologously obtained from a platelet preparation of a patient and used to cultivate primary cells from the same patient for transplantation in the patient, reducing the patient's exposure to xenogenic/allogenic compounds and subsequent immunological reactions.

In embodiments, a wound healing composition comprises a lyophilized platelet lysate composition comprising a supplemental growth factor and has a water content of 50% or less, and optionally, at least 0.1 mM calcium. In embodiments, a method comprises administering a wound healing composition that comprises a lyophilized platelet lysate composition and an aqueous solvent having at least 0.1 mM calcium to a wound.

The basal medium, cell culture medium supplements, and/or amount of PL to include in the cell culture medium composition can be selected or determined using conventional methods. The basal medium can be selected based on the type of cells to be cultured. For example, HUVEC cells can be cultured in EBM™-2 (Lonza; Walkersville, MD), MCDB-131 DMEM/F-12, and M199 mediums.

The cell culture medium composition can be prepared with different combinations of basal media and cell culture medium supplements. The percent confluence of the cells in the media compositions can be compared and the combination which provides the fastest proliferation rate and/or the highest percent confluence can be selected. The proliferation rate or the percent confluence may be determined by seeding a defined number of cells which is the same for each condition, counting the cell number (for proliferation rate) and the surface area occupied by cells (for confluence) at different time points after seeding and comparing the proliferation rates and percent confluence from the different conditions.

EC growth can be measured by standard cell proliferation assays. One example of such an assay is the commonly used BrdU method. This assay method detects 5-bromo-2'-deoxyuridine (BrdU) incorporated into cellular DNA during cell proliferation using an anti-BrdU antibody. When EC are cultured with labeling medium that contains BrdU, this pyrimidine analog is incorporated in place of thymidine into the newly synthesized DNA of proliferating cells. After removing labeling medium, cells are fixed and the DNA is denatured and then a BrdU mouse mAb is added to detect the incorporated BrdU. A detection antibody is then used to recognize the bound detection antibody and to develop color. The magnitude of the absorbance for the developed color is proportional to the quantity of BrdU incorporated into cells, which is a direct indication of cell proliferation.

Growth and/or proliferation of EC cells can also be determined by measuring cell confluence. Cultured human EC form a monolayer adhered to the surface of cell culture vessels, similar to their biology in vivo. Thus, in cell culture, EC growth can be directly assessed by measuring percentage confluence of the cells within a given surface area of the culture vessel. In a typical assay, human EC or EPC are grown in a cell culture medium composition according to the disclosure. At suitable passages, (e.g., either passage 4 or 5), cells are harvested (medium removed, cells rinsed with HEPES buffered saline, cells detached with trypsin/EDTA, and the trypsin neutralized with trypsin neutralizing solution), collected by centrifugation, and plated in a cell culture vessel with indicated seeding density. After 24 hours, the medium in each flask or in each well is completely replaced with fresh cell culture medium. Then, the growth of the cells is monitored with, for example, an IncuCyte instrument, a remotely controlled microscope contained inside of the incubator. By taking pictures of EC monolayer and analyzing the images, the instrument provides quantitative and comprehensive invasive measurements of the cell monolayer image-based confluence metrics calculated across multiple regions of a cell culture vessel. The media is completely replaced after another 48 hours of culture, and the cultures are monitored for a total of 60 to 100 hours. The growth curves are generally plotted as plots of percent confluence, as measured by the software of the IncuCyte instrument, with time of culture, after the initial 24 hours.

The health of cultured EC or EPC can be detected by visual inspection of the morphological changes of the monolayer. Detachment of EC or EPC from the surface of culture vessel and the resulting decline in percentage confluence usually signals deterioration of the health of cultured EC or EPC. Alternatively, standard cell toxicity assays can be used to more accurately measure EC toxicity and viability, such as the commonly used MTT assay. The MTT (3-(4,5-dimethylthiazol-2-yl)-2,5-diphenyltetrazolium bromide) tetrazolium reduction assay has been widely adopted and remains popular in academic labs. The MTT substrate is prepared in a physiologically balanced solution, added to cells in culture, and incubated for 1 to 4 hours. The quantity of formazan (presumably directly proportional to the number of viable cells) is measured by recording changes in absorbance at 570 nm using a plate reading spectrophotometer. Viable cells with active metabolism convert MTT into a purple colored formazan product with an absorbance maximum near 570 nm. When cells die, they lose the ability to convert MTT into formazan, thus color formation serves as a useful and convenient marker of only the viable cells.

Standard cell assays that are commonly used in drug screening for immunogenicity can be adopted to test immunogenicity in the cell culture media compositions of the disclosure. For example, a dendritic cell-T cell assay (DC-T) (ProImmune) can be used when different media (for example PL+FGF v. FBS v. serum-free media) are added to DC-T, and CD4+ T cell proliferation is used as indication for immunogenicity. Higher T cell proliferation indicates higher immunogenicity. Toxicity in cell culture can also be determined or monitored by microscopic observation of the cultured cells.

Morphological alterations in cells exposed to media containing toxic materials can be compared and correlated to standard cell viability assays such as MTT or MTS assays. Inappropriate differentiation involves abnormal cell proliferation rate, unnatural cell morphology and change of cell phenotype compared to freshly isolated and cultured primary human EC. When cultured under different media conditions (for example, PL+FGF v. FBS v. serum-free media), proliferation rate of the cultured cells can be determined, for example, by microscopic imaging analysis or with BrdU method; cell morphology can be ascertained by microscopic imaging analysis; phenotypic change in primary EC can be determined by examination of typical human EC cell surface markers (e.g., CD31, VCAM-1, ICAM-1, etc.) by established methods, such as flow cytometry and cell surface ELISA.

EXAMPLES

The present disclosure can be best understood in conjunction with the following nonlimiting examples, which are intended to illustrate the cell culture media, compositions and methods described herein. It will be understood that other aspects, advantages, and modifications are within the scope of the following claims.

Example 1

Platelet Lysate is Superior to FBS to Culture EC

This example demonstrates that platelet lysate (PL) provides improved primary human endothelial cell (EC) growth and maintenance properties as compared to fetal bovine serum (FBS). The growth characteristics of primary endothelial cells cultured with media supplemented with a platelet lysate (PL) were compared to cells cultured with media supplemented with fetal bovine serum (FBS). FBS is a commonly used supplement for culturing endothelial cells in vitro for research purposes. However, FBS is derived from animal products and thus severely limits the use of endothelial cell culture for clinical applications.

Here we show that substitution of PL for FBS produced superior growth characteristics for primary endothelial cell culture. Because PL is made from human platelets under cGMP compatible processes, serum-free media containing PL can be used to culture cells, including human endothelial cells (hECs) and human endothelial progenitor cells (hEPCs), for clinical applications.

Primary human umbilical vein endothelial cells (HUVECs; Lonza Walkersville, Inc.; Walkersville, MD) were grown in EGM™-2 media (Lonza) supplemented with PL or FBS. EGM™-2/PL media was made by mixing EGM™-2 media (i.e., EBM™-2 basal medium supplemented with the SingleQuots™ components hEGF, hFGF-B, R3-IGF-1, VEGF, ascorbic acid, heparin, hydrocortisone, and GA-1000 (Gentamicin, Amphotericin-β) (Lonza Walkersville, Inc.; Walkersville, MD) and PL at a final concentration of 2% (v/v). HUVECs from the same donors were also cultured, under the same conditions, with EGM™-2/FBS media (i.e., EGM™-2 media supplemented with 2% FBS (v/v). In some experiments, EGM™-2/FBS was made by mixing EGM™-2 media and FBS at a final concentration of 2% (v/v).

At passage 4 or 5, HUVECs were harvested, media was removed, cells were 15 rinsed with HEPES buffered saline and detached from culture plates with trypsin/EDTA, and the trypsin was neutralized. HUVECs were collected by centrifugation (200×g for 5 min at room temperature) and plated at $2.5 \times 10^3$ cells/cm$^2$ in a T-25 flask or at $5.0 \times 10^3$ cells/cm$^2$ in wells of a 48-well plate. After 24 hours, the medium in each flask or well was replaced with fresh medium. HUVEC cell growth was continuously monitored with an IncuCyte instrument (Essen BioScience; Ann Arbor, MI), a remotely controlled microscope housed within an incubator. After an additional 48 hours, the medium in each flask or well was replaced and the cultures were monitored for a total of 64-80 hours.

The growth curves, which are presented in FIG. 1, are plots of percent HUVEC confluence as a function of time in culture after an initial period of 24 hours. Data are from one T-25 flask per growth condition or the average of six wells of a 48-well plate per growth condition. As shown in FIG. 1, HUVECs exhibited superior growth rates in EGM™-2 medium supplemented with 2% PL as compared to EGM™-2 medium supplemented with 2% FBS while achieving the same level of confluence in both media.

As shown in FIG. 2, human umbilical vein endothelial cells (HUVECs) cultured in EGM™-2 basal media (no FBS or SingleQuots supplement) with added PL exhibited excellent growth characteristics whereas HUVEC did not grow in EGM™-2 basal media without added PL. These data demonstrate, therefore, that PL was critical for robust growth of those endothelial cells.

Example 2

EBM™-2 Basal Medium Supplemented with Platelet Lysate and FGF-B Support the Growth of HUVECs in Culture This example demonstrates HUVECs exhibit superior growth characteristics in either EGM™-2 media supplemented with platelet lysate (PL) or in EBM™-2 basal medium supplemented with PL and the cytokine, human basic fibroblast growth factor (FGF-B), as compared to EGM™-2 media supplemented with FBS.

EGM™-2 media, which is commonly used in combination with FBS for the culture in EC and EPC, is prepared by supplementing EBM™-2 basal media with SingleQuots™ (Lonza Walkersville, Inc.; Walkersville, MD) a media supplement containing a combination of nine cytokines, chemicals, hormones, and antibiotics. The SingleQuots™ supplement includes the growth factors hEGF, hFGF-B, R3-IGF-1, and VEGF; the chemicals ascorbic acid and heparin; the steroid hormone hydrocortisone; and the antibiotics Gentamicin and Amphotericin-B. The SingleQuots™ combination may, however, detrimentally affect the biology of primary ECs and EPCs and, therefore, can restrict the clinical utility of ECs and EPCs cultured in, e.g., EBM™-2 media supplemented with SingleQuots™.

The growth characteristics of primary human umbilical vein endothelial cells (HUVECs) cultured in EGM™-2 basal media (no FBS or SingleQuots supplement) supplemented with PL, EGM™-2 basal media EGM™-2 supplemented with PL in further combination with recombinant human basic fibroblast growth factor (FGF-B) were compared to the growth characteristics of primary HUVECs cultured in EGM™-2 media supplemented with only FBS. Primary human umbilical vein endothelial cells (HUVECs) were plated in EGM™-2 basal media supplemented with 2% PL, EGM™-2 basal media supplemented with FBS, and in EBM™-2 basal media supplemented with 2% PL and 10 ng/ml FGF-B and the growth of the plated HUVECs was continuously monitored for 80 hours. The FGF-B used in these experiments can be obtained from the SingleQuots supplement or from CellGenix.

The growth curves presented in FIG. 3 show the percent confluence of HUVECs, as measured by an IncuCyte kinetic imaging instrument, as a function of time in culture (from 0 to 72 hours). This data demonstrates that HUVECs cultured in EBM™-2 media supplemented with PL and FGF-B exhibited comparable growth characteristics as compared to HUVECs cultured in EBM™-2 media supplemented FBS.

Figure 4:
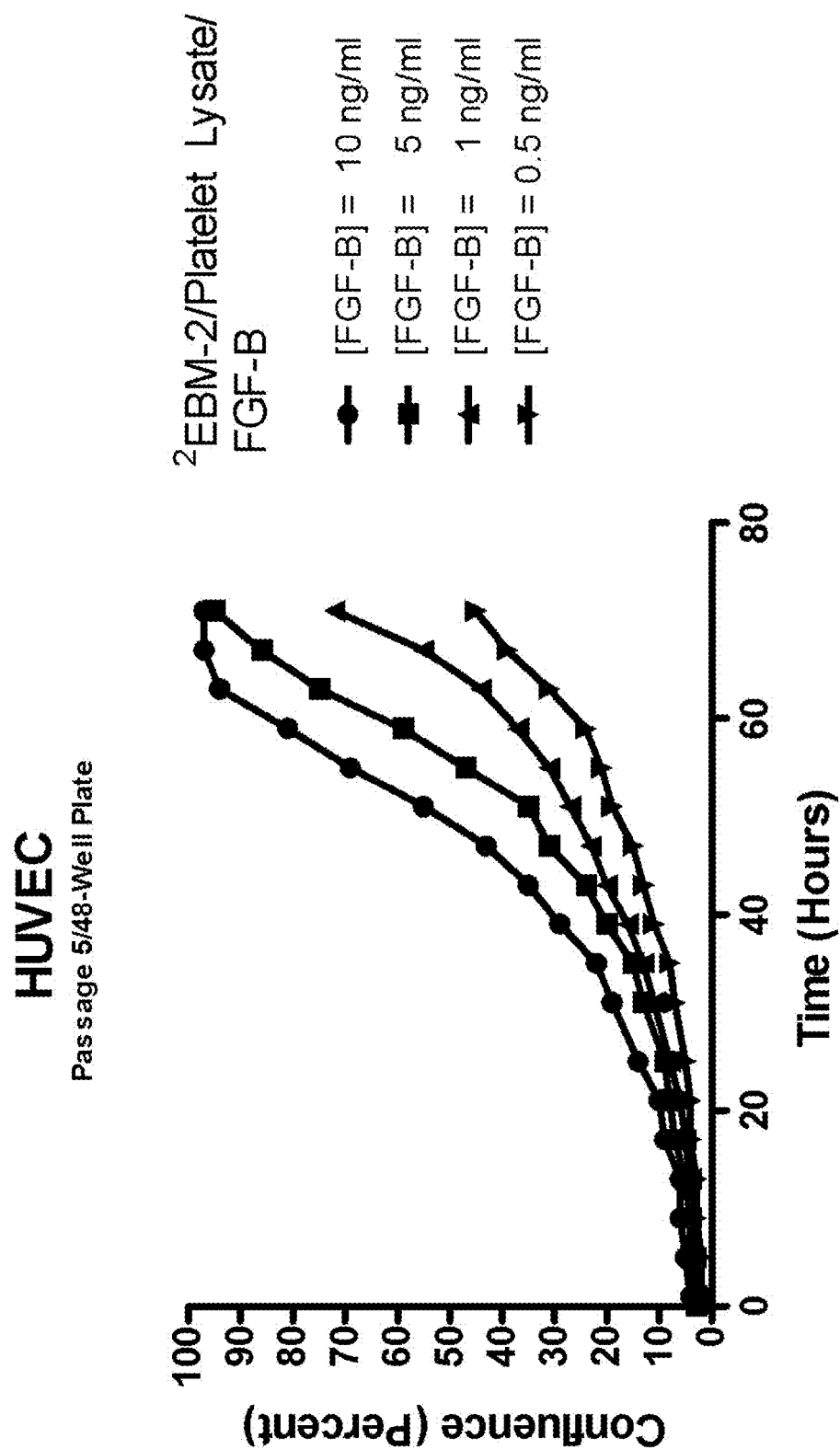
FIG. 4 is a graph of percent confluence as a function of time (from 0 to 72 hours) for human umbilical vein endothelial cells (HUVEC) plated onto 48-well plates containing EBM™-2 media supplemented with PL and FGF-B at 10 ng/ml (●), 5 ng/ml (■), 1 ng/ml (▲), and 0.5 ng/ml (▼), which demonstrates that HUVEC growth characteristics improve as a function of increasing FGF-B concentration.

The growth curves presented in FIG. 4 show the percent confluence of HUVECs as a function of time in culture (from 0 to 72 hours) for HUVECs cultured in EBM™-2 basal media supplemented with 2% PL and FGF-B at 10 ng/ml, 5 ng/ml, 1 ng/ml, and 0.5 ng/ml. This data demonstrates that HUVECs cultured in EBM™-2 basal media supplemented with PL exhibit FGF-B-dependent growth characteristics that become increasingly robust with increasing concentration of FGF-B. Moreover, when cultured with 5 ng/ml and 10 ng/mL FGF-B, HUVECs achieved greater than 90% confluence at approximately 72 hours, while HUVECs cultured with 0.5 ng/ml and 1 ng/ml FGF-B achieved 45% and 70% confluence, respectively, at approximately 72 hours.

In total, the data presented in this Example demonstrate that the combination of PL and FGF-B can replace FBS and SingleQuots™ as a supplement of basal media (e.g., EBM™-2) to generate cell culture media compositions that support the robust growth characteristics of endothelial cells (ECs) and endothelial progenitor cells (EPCs).

Example 3

Basal Media Supplemented with Platelet Lysate and FGF-B Support the Growth of HUVECs in Culture This example demonstrates that a variety of basal media, when supplemented with PL and the growth factor FGF-B, support the growth characteristics of endothelial cells (ECs), including endothelial progenitor cells (EPCs), in culture. In particular, the growth characteristics of HUVECs in the EBM™-2 basal medium supplemented with PL and FGF-B were compared to the growth characteristics of HUVECs in the basal medium MCDB-131 and the restrictive basal medium DMEM/F-12 also supplemented with PL and FGF-B.

The compositions of MCDB-131 and DMEM/F-12 are presented herein as available from Life Technologies Corp. (Grand Island, NY). In some experiments, the MCDB-131 media was supplemented with 2% PL and FGF-B (CellGenix) is also supplemented with heparin, ascorbic acid, hydrocortisone, GA-1000, among others. In some experiments, was DMEM/F-12 media supplemented with 2% PL and FGF-B (CellGenix) is also supplemented with heparin, ascorbic acid, hydrocortisone, GA-1000, among others.

Figure 5:
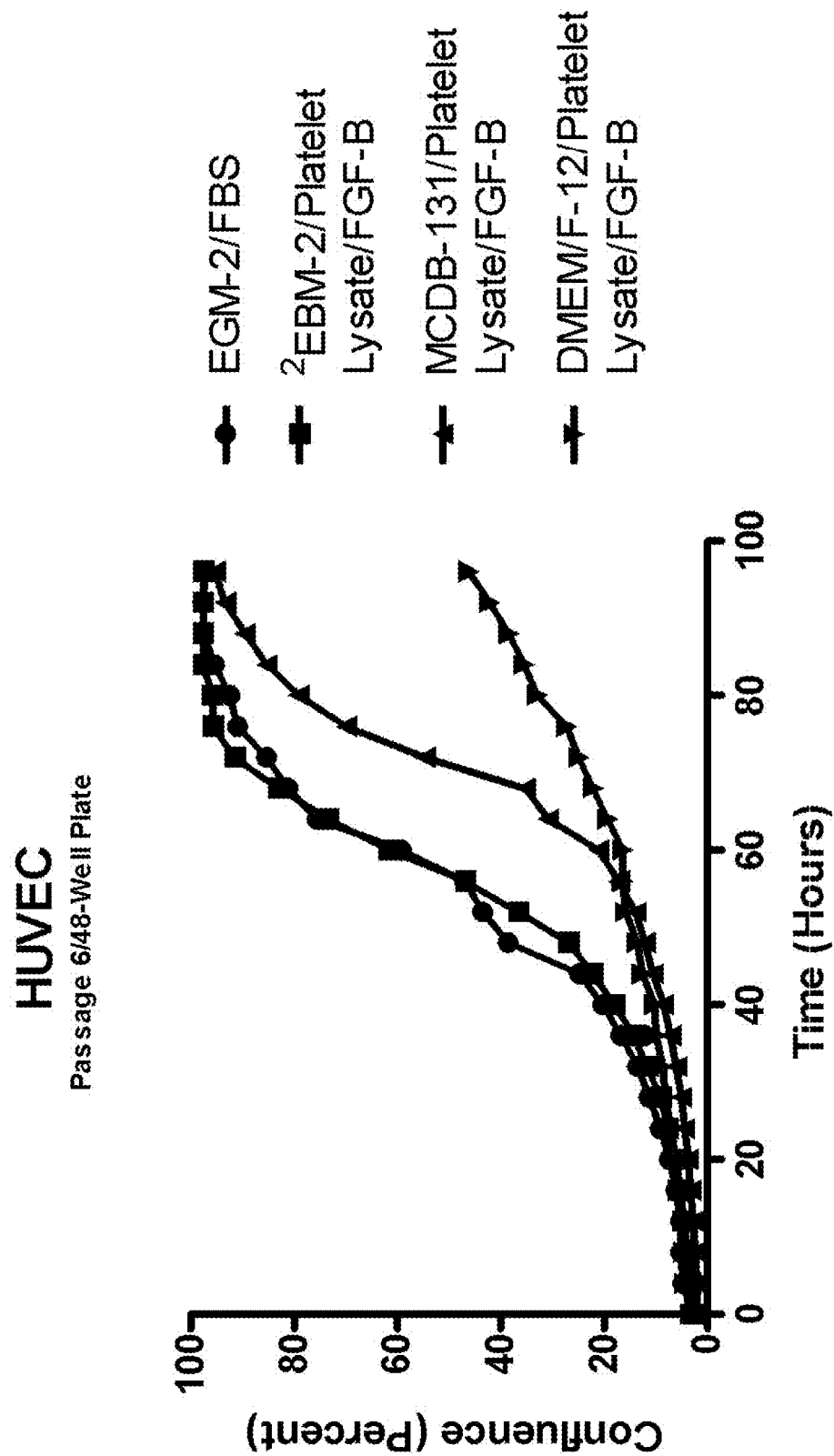
FIG. 5 is a graph of percent confluence as a function of time (from 0 to 100 hours) for human umbilical vein endothelial cells (HUVEC) plated onto 48-well plates containing EGM-2 medium 15 supplemented with FBS (●), EBM-2 basal medium supplemented with PL and FGF-B (■), MCDB-131 basal medium supplemented with PL and FGF-B (▲), and DMEM/F-12 restrictive basal medium supplemented with PL and FGF-B (▼), which demonstrate that the basal medium MCDB-131 and the restrictive basal medium DMEM-F-12, when supplemented with PL and FGF-B, both support HUVEC growth characteristics.

HUVECs were plated in each basal media (EBM-2, MCDB-131, and DMEM-F-12) supplemented with 2% PL and in EGM-2 supplemented with 2% FBS and the growth of the HUVECs was continuously monitored for up to 100 hours. Growth curves showing percent confluence, as measured by an IncuCyte kinetic imaging instrument, as a function of time for HUVECs plated in 48-well plates (average of six wells of a 48-well plate per growth condition) are presented in FIG. 5.

HUVECs plated in the basal medium MCDB-131 supplemented with PL and FGF-B exhibited slightly slower growth rates but achieved equivalent confluence (>95% after 96 hours) as compared to EBM-2 supplemented with 2% PL and 10 ng/ml FGF-B. By comparison, HUVECs plated in the restrictive basal medium DMED-F-12 supplemented with PL and FGF-B exhibited substantially slower, but significant, growth rates, and did not achieve confluence after 100 hours as compared to EBM-2 supplemented with 2% PL and 10 ng/ml FGF-B.

Example 4

Lyophilized Platelet Lysate Supports the Growth Characteristics of Mesenchymal Stem Cells (MSCs) in Culture This example demonstrates that cell culture media compositions prepared with lyophilized human PL support the growth characteristics of cultured cells in a manner that is comparable to cell culture media compositions prepared with non-lyophilized PL.

To prepare the lyophilized human PL, aliquots of thawed human PL were frozen as 5 shells using a dry ice-ethanol bath and lyophilized overnight. An equal volume of the same platelet lysate was re-frozen but not lyophilized. The lyophilized samples were reconstituted with sterile water at room temperature for 15 minutes to the same final volume as the prelyophilized volume. The re-frozen, non-lyophilized samples were incubated in a 37° C. water bath until just thawed. Both the lyophilized and non-lyophilized samples were incubated in a 37° C. water bath for 15 minutes and centrifuged at 1,800×g for ten minutes at room temperature. The centrifugation step produced a clear supernatant with a floating layer and a pelleted clot-like precipitate. The clear supernatant and the floating layer were retained and incorporated into the cell culture medium. The lyophilized samples were slightly more turbid than the non-lyophilized samples. The protein concentration of three platelet lysate preparations was determined by measuring the A280, corrected for Rayleigh light scattering. Recovery of protein content ranged from 85%-95% for lyophilized samples.

Mesenchymal stem cells (MSCs), generated in the Human Cell Therapy Laboratory at Mayo Clinic, were plated in either 12- or 24-well Corning/Costar tissue culture plates at $2.5 \times 10^3$ cells/cm2 in the respective medium, composing advanced MEM with GlutaMAX, heparin, penicillin/streptomycin with 5% lyophilized or non-lyophilized human PL. Cell growth was continuously monitored for up to 100 hours.

Figure 6B:
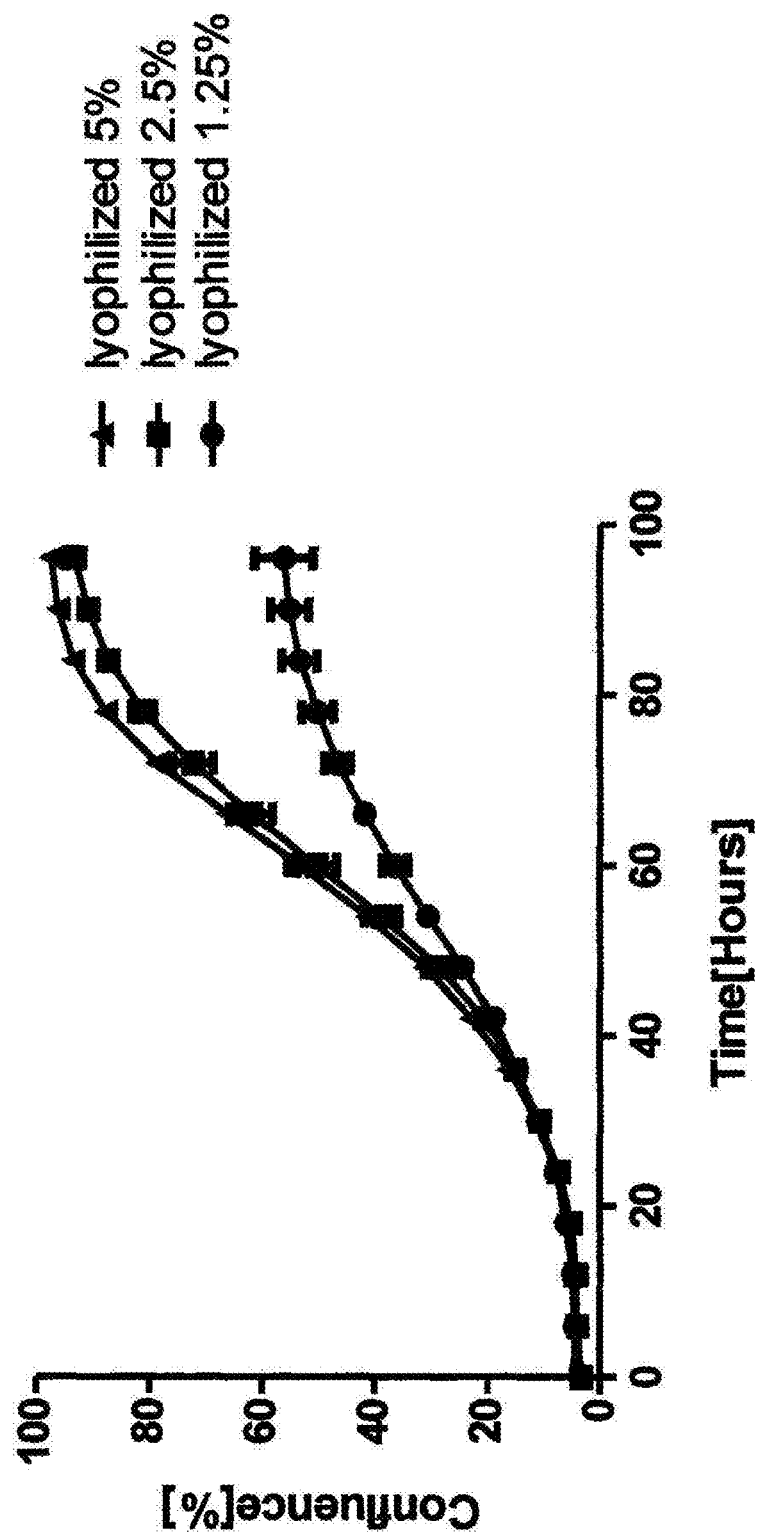
FIG. 6B is a graph of percent confluence as a function of time (from 0 to 100 hours) for mesenchymal stem cells (MSCs) plated onto 48-well plates containing advance MEM with GlutaMAX, heparin, and penicillin/streptomycin further supplemented with PL (lyophilized) at concentrations of 5% (v/v) (▲), 2.5% (v/v) (■), and 1.25% (v/v) (●). These data demonstrate that the growth characteristics of MSCs in advance MEM with GlutaMAX, heparin, and penicillin/streptomycin further supplemented with lyophilized PL are substantially identical to the growth characteristics of MSCs in advance MEM with GlutaMAX, heparin, and penicillin/streptomycin further supplemented with non-lyophilized PL. Moreover, because substitution of lyophilized PL for non-lyophilized PL yielded substantially identical growth characteristics for cultured MSC cells, these data further demonstrate that lyophilization of PL does not affect the biological activity of components within PL that support cell growth.

The growth curves presented in FIGS. 6A and 6B show percent confluence, as measured by an IncuCyte kinetic imaging instrument, as a function of time in culture. These data are from an average of six wells of a 24-well plate per growth condition. Advance MEM with GlutaMAX, heparin, and penicillin/streptomycin was further supplemented with PL (non-lyophilized in FIG. 6A and lyophilized in FIG. 6B) at concentrations of 5% (v/v), 2.5% (v/v), and 1.25% (v/v). Even at the lowest concentration tested (1.25% (v/v)) lyophilized PL was able to promote growth characteristics of MSC cells in a manner comparable to non-lyophilized PL. Moreover, because substitution of lyophilized PL for non-lyophilized PL yielded substantially identical growth characteristics for cultured MSC cells, these data further demonstrate that lyophilization of PL does not affect the biological activity of components within PL that support cell growth.

Although lyophilization is a useful technique for single recombinant proteins, the ability to lyophilize a complex protein mixture, such as PL, that retains its growth properties after lyophilization was unexpected and surprising. Desiccation is known to eliminate or reduce the infectiousness of viruses and some bacteria. Thus, lyophilization can be used to improve the safety profile of the PL. In addition, lyophilization can be used to improve the storage and transportation parameters of the PL, reducing the temperature required for storage and transportation and increasing the life span of proteins.

Figure 9:
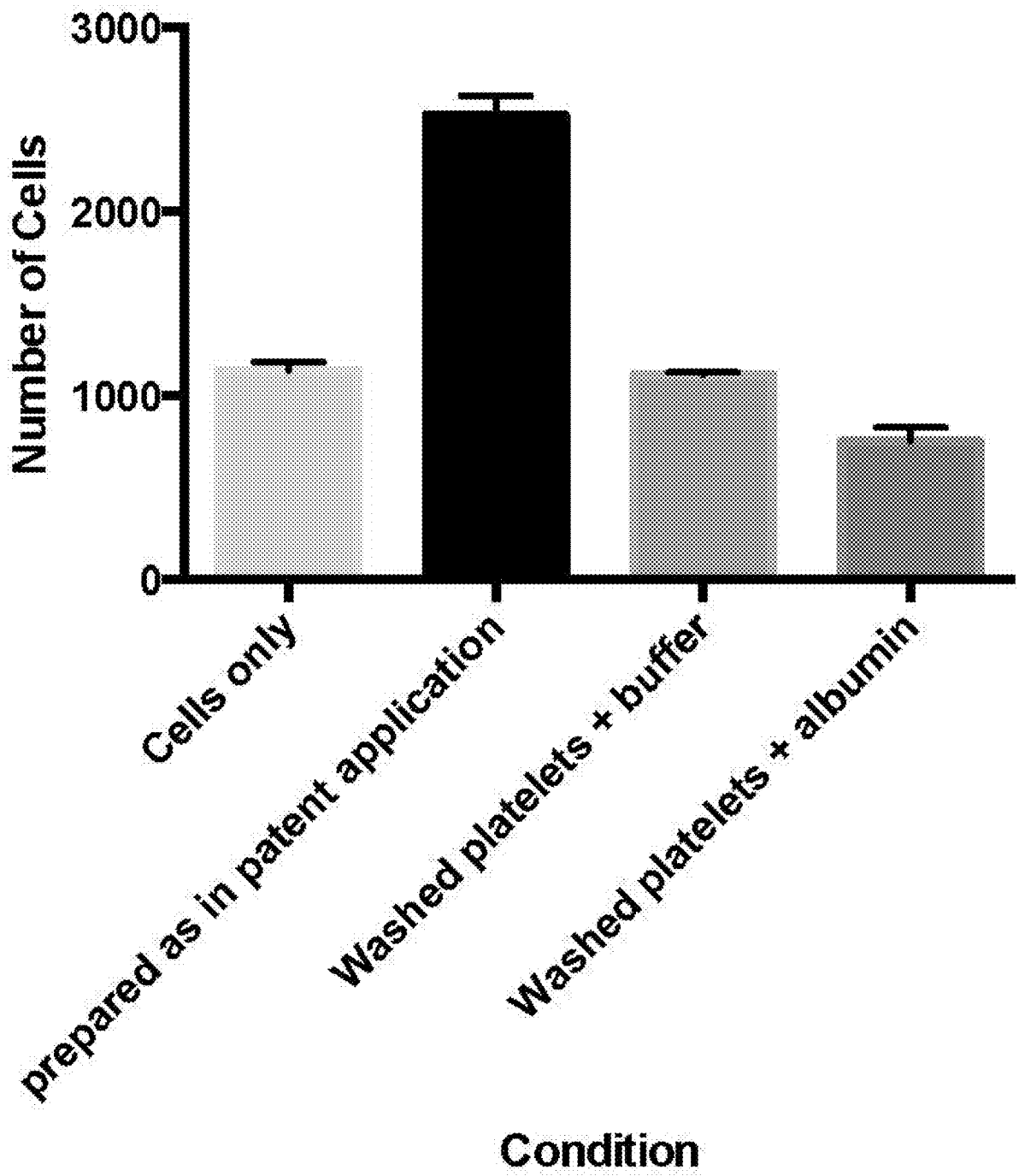
FIG. 9 is a graph showing that a PL composition including an anticoagulant enhanced the growth of mesenchymal stem cells while washed platelets and washed platelets with albumin did not provide for growth of these cells.

In addition, the growth of mesenchymal stem cells cultured in the presence of P1, washed intact or unlysed platelets plus buffer, washed intact or unlysed platelets plus albumin. The results are shown in FIG. 9. The results show that only the PL enhanced growth of mesenchymal stem cells over control.

What is claimed is:

1. A wound healing composition comprising:
   a lyophilized platelet lysate having 50% or less of water; and
   a supplemental exogenous growth factor in a ratio of at least 100 to 1 or less per ng of growth factor in the platelet lysate.

2. The wound healing composition of claim 1, further comprising an anticoagulant.

3. The wound healing composition of claim 2, wherein the anticoagulant is selected from the group consisting of heparin, heparin derivatives, EDTA, citrate, oxalate, and combinations thereof.

4. The wound healing composition of claim 1, further comprising about 0.1 mM to 100 mM calcium.

5. The wound healing composition of claim 1, wherein the supplemental exogenous growth factor is FGF.

6. The wound healing composition of claim 1, wherein the wound healing composition is free from bulking agents selected from the group consisting of sucrose, mannitol, trehalose, and combinations thereof.

7. The wound healing composition of claim 1, wherein the wound healing composition is free from animal serum.

8. The wound healing composition of claim 1, further comprising one or more selected from the group consisting of one or more amino acids, an energy source, one or more vitamins, one or more inorganic salts, and combinations thereof.

9. The wound healing composition of claim 1, wherein the wound healing composition further comprises from about 200 to about 1600 mg/L amino acids, from about 20 to about 50 mg/L vitamins, from about 6000 to about 8000 mg/L inorganic salts, and from about 800 to about 3500 mg/L glucose.

10. The wound healing composition of claim 1, further comprising glucose.

11. The wound healing composition of claim 1, further comprising MCDB-131, DMEM/F-12, or EBM-2.

12. The wound healing composition of claim 1, wherein the supplemental exogenous growth factor is fibroblast growth factor (FGF-B), epidermal growth factor (EGF), platelet derived growth factor (PDGF), insulin-like growth factor (IGF), transforming growth factor (TGF), vascular endothelial growth factor (VEGF), liver growth factor (LGF), bone morphogenetic protein (BMP), colony stimulating factor (CSF), hepatocyte growth factor (HGF), nerve growth factor (NGF), or combinations thereof.

13. The wound healing composition of claim 1, wherein the lyophilized platelet lysate comprises a total protein concentration of at least 30 mg/ml.

14. A method of administering a wound healing composition, comprising applying the wound healing composition of claim 1 to a wound.

* * * * *